(12) United States Patent
Kaupp et al.

(10) Patent No.: US 8,765,103 B2
(45) Date of Patent: *Jul. 1, 2014

(54) PEARLESCENT PIGMENTS CONTAINING COSMETIC COMPOSITIONS

(75) Inventors: Günter Kaupp, Neuhaus (DE); Ulrich Schmidt, Hersbruck (DE); Katrin Steinbach, Nürnberg (DE); Dirk Schumacher, Pegnitz (DE)

(73) Assignees: Glassflake Limited (GB); Eckart GmbH (DE)

( * ) Notice: Subject to any disclaimer, the term of this patent is extended or adjusted under 35 U.S.C. 154(b) by 5 days.

This patent is subject to a terminal disclaimer.

(21) Appl. No.: 12/594,509

(22) PCT Filed: Apr. 4, 2008

(86) PCT No.: PCT/EP2008/002712
§ 371 (c)(1),
(2), (4) Date: Oct. 2, 2009

(87) PCT Pub. No.: WO2008/122421
PCT Pub. Date: Oct. 16, 2008

(65) Prior Publication Data
US 2010/0047300 A1 Feb. 25, 2010

(30) Foreign Application Priority Data
Apr. 5, 2007 (EP) .................... 07007257

(51) Int. Cl.
*A61K 8/25* (2006.01)
*A61Q 1/02* (2006.01)
*A61Q 3/02* (2006.01)
*A61K 8/02* (2006.01)
*A61K 8/26* (2006.01)
*A61K 8/28* (2006.01)
*A61K 8/29* (2006.01)

(52) U.S. Cl.
CPC ............. *A61K 8/0258* (2013.01); *A61K 8/25* (2013.01); *A61K 8/26* (2013.01); *A61K 8/28* (2013.01); *A61K 8/29* (2013.01)
USPC ............................................ 424/63; 106/489

(58) Field of Classification Search
None
See application file for complete search history.

(56) References Cited

U.S. PATENT DOCUMENTS

| | | |
|---|---|---|
| 3,087,828 A | 4/1963 | Linton et al. |
| 3,711,308 A | 1/1973 | Brand et al. |
| 3,832,208 A | 8/1974 | Jackson |
| 3,874,890 A | 4/1975 | Bernhard et al. |
| 3,926,659 A | 12/1975 | Bernhard et al. |
| 4,086,100 A | 4/1978 | Esselborn et al. |
| 4,456,486 A | 6/1984 | Bernhard |
| 4,457,784 A | 7/1984 | Bernhard |
| 4,494,993 A | 1/1985 | Bernhard et al. |
| 4,509,988 A | 4/1985 | Bernhard |
| 4,537,636 A | 8/1985 | Bernhard et al. |
| 4,565,581 A | 1/1986 | Bernhard |
| 5,433,779 A | 7/1995 | DeLuca, Jr. |
| 5,496,565 A | 3/1996 | Heinze et al. |
| 5,921,778 A * | 7/1999 | Karmaker et al. ............ 433/215 |
| 5,958,125 A | 9/1999 | Schmid et al. |
| 6,132,873 A | 10/2000 | Dietz et al. |
| 6,596,070 B1 | 7/2003 | Schmidt et al. |
| 7,597,900 B2 * | 10/2009 | Zimmer et al. ............... 424/401 |
| 2001/0001174 A1 | 5/2001 | Andes et al. |
| 2001/0021388 A1 | 9/2001 | Motitschke et al. |
| 2004/0091433 A1 | 5/2004 | Buchholz et al. |
| 2004/0220137 A1 | 11/2004 | Sauermann |
| 2006/0042508 A1 | 3/2006 | Henglein et al. |
| 2006/0042509 A1 | 3/2006 | Henglein et al. |
| 2006/0166806 A1 * | 7/2006 | Fechner et al. .................. 501/45 |
| 2006/0225609 A1 | 10/2006 | Rueger et al. |
| 2006/0251883 A1 * | 11/2006 | Ogawa et al. ................. 428/328 |
| 2007/0225424 A1 * | 9/2007 | Schulz et al. ................. 524/494 |
| 2009/0311209 A1 * | 12/2009 | Bujard ............................ 424/63 |
| 2010/0116169 A1 | 5/2010 | Kaupp et al. |

FOREIGN PATENT DOCUMENTS

| | | |
|---|---|---|
| DE | 14 67 468 | 12/1968 |
| DE | 19 59 998 | 7/1971 |
| DE | 20 09 566 | 11/1971 |
| DE | 22 14 545 | 10/1972 |

(Continued)

OTHER PUBLICATIONS

Notice of Reasons for Rejection dated May 21, 2013 in corresponding Japanese Patent Application No. 2010-501441 (English language translation).
Mori Masahiro, VIII, Glass no Kakuron, Glass Kogaku Handbook, Kunizo Asakura, Asakura Publishing Co., Ltd., 1997, First Version, pp. 513-519 (Japanese language).
International Search Report dated Jul. 7, 2008, issued in corresponding international application No. PCT/EP2008/002712.
European Report dated Sep. 14, 2007, issued in corresponding European priority application No. 07007257.4.
Morten C. Mgilgaard/Gail Vance Civille/B. Thomas Carr "Sensory Evaluation Techniques," CRC Press, 4th ed., Chapter 7: Attribute Difference tests, (2006, 4th ed.).

*Primary Examiner* — H. Sarah Park
(74) *Attorney, Agent, or Firm* — Ostrolenk Faber LLP

(57) ABSTRACT

The present invention is directed to a cosmetic composition comprising an effect pigment based on a glass flake as a substrate with a coating, said coating comprising at least one layer of at least one high refractive material, said material having a refractive index of at least 1.8, and/or a semitransparent metal coating wherein said glass flakes comprising the following composition: 65-75 wt.-% silicon oxide, preferably $SiO_2$ 2-9 wt.-% aluminium oxide, preferably $Al_2O_3$ 0.0-5 wt.-% calcium oxide, preferably CaO 5-12 wt.-% sodium oxide, preferably $Na_2O$ 8-15 wt.-% boron oxide, preferably $B_2O_3$ 0.1-5 wt.-% titanium oxide, preferably $TiO_2$ 0.0-5 wt.-% zirconium oxide, preferably $ZrO_2$ based on the weight of said glass flakes. The invention is also directed to the use of the cosmetic composition.

19 Claims, 2 Drawing Sheets

(56) References Cited

FOREIGN PATENT DOCUMENTS

| | | |
|---|---|---|
| DE | 22 15 191 | 10/1972 |
| DE | 22 44 298 | 3/1974 |
| DE | 23 13 331 | 9/1974 |
| DE | 25 22 572 | 12/1976 |
| DE | 31 37 808 | 3/1983 |
| DE | 31 37 809 | 3/1983 |
| DE | 31 51 343 | 7/1983 |
| DE | 31 51 354 | 7/1983 |
| DE | 31 51 355 | 7/1983 |
| DE | 32 11 602 | 10/1983 |
| DE | A-43 08 282 | 9/1994 |
| DE | EP-A-0 671 161 | 9/1995 |
| DE | 196 18 566 A1 | 11/1997 |
| DE | 196 38 708 | 4/1998 |
| DE | 199 07 313 A1 | 8/2000 |
| DE | A-101 33 202 | 1/2003 |
| DE | A-102 32 595 | 2/2004 |
| DE | 10 2004 041 586 | 3/2006 |
| DE | 10 2004 041 592 A1 | 3/2006 |
| DE | 10 2005 029 647 A1 | 2/2007 |
| EP | 0 289 240 A1 | 11/1988 |
| EP | 0753 545 A2 | 1/1997 |
| EP | 0912 640 B1 | 3/2000 |
| EP | 1 025 168 B1 | 8/2000 |
| EP | 1 725 301 A1 | 11/2006 |
| EP | 1 893 302 A1 | 3/2008 |
| GB | 1359933 A | 4/1974 |
| JP | 60-260443 | 12/1985 |
| JP | 7-246366 | 9/1995 |
| JP | 2006-510797 | 3/2006 |
| JP | 2008-546880 | 12/2008 |
| WO | WO 97/46624 A | 5/1999 |
| WO | WO 2004/056716 A1 | 7/2004 |
| WO | WO 2005/063637 | 7/2005 |
| WO | WO 2005/092281 | 10/2005 |
| WO | WO 2006/021388 A | 3/2006 |
| WO | WO 2006/136386 A | 12/2006 |
| WO | WO 2007054379 A1 * | 5/2007 |

* cited by examiner

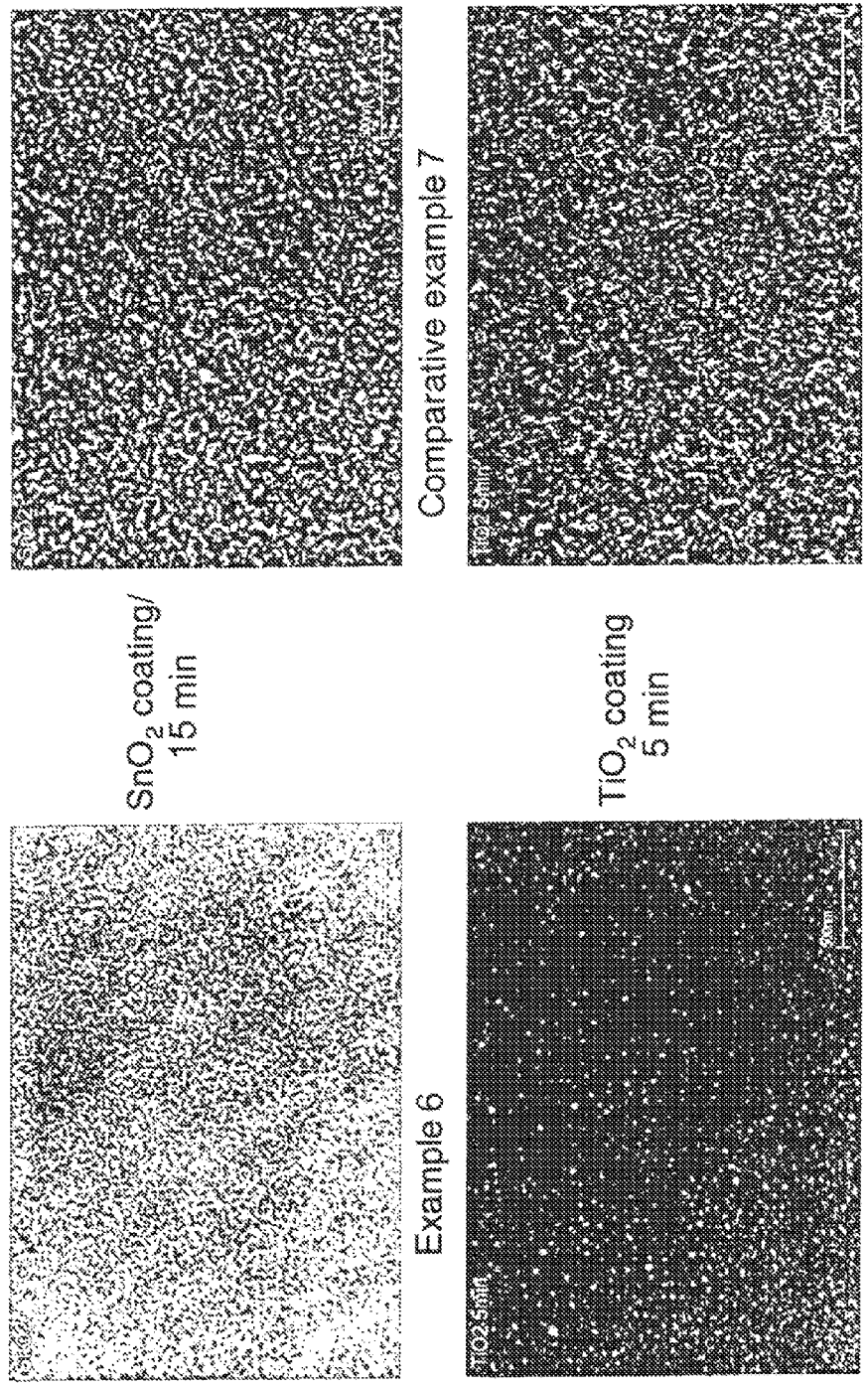

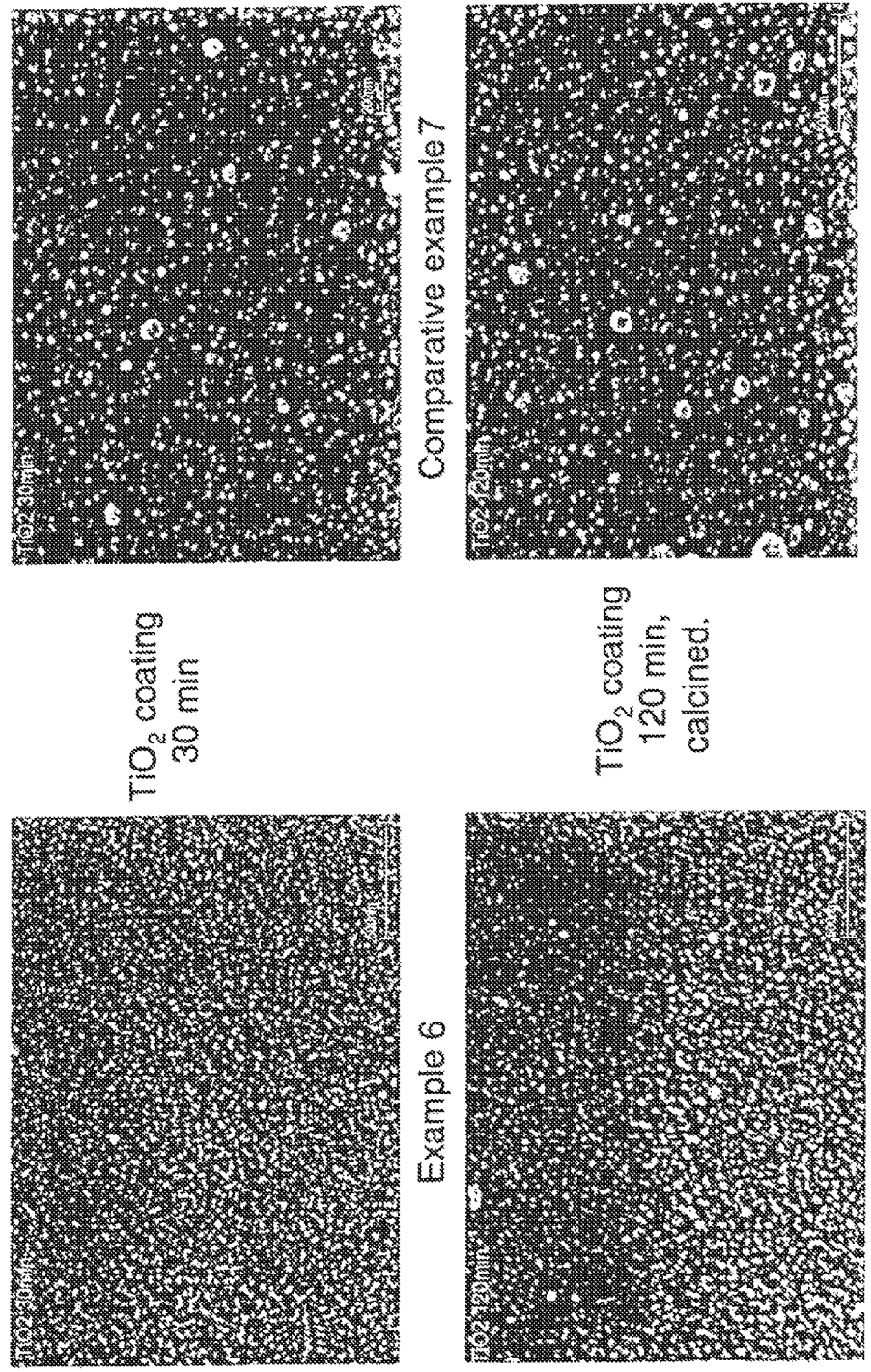

PEARLESCENT PIGMENTS CONTAINING COSMETIC COMPOSITIONS

CROSS REFERENCE TO RELATED APPLICATIONS

The present application is a 35 U.S.C. §371 National Phase conversion of PCT/EP2008/002712, filed Apr. 4, 2008, which claims benefit of European Application No. 07007257.4, filed Apr. 5, 2007, the disclosure of which is incorporated herein by reference. The PCT International Application was published in the English language.

TECHNICAL FIELD

The present invention is directed to a cosmetic composition comprising effect pigments.

BACKGROUND OF THE INVENTION

Pearlescent pigments are increasingly used in cosmetic preparations due to their very decorative optic properties.

EP 0 912 640 B1 discloses a pearlescent pigment comprising flakes of C glass having a first coating comprising iron oxide or rutile titanium dioxide thereon. The skilled person reads from EP 0 912 640 B1 that flakes of C glass are the only glass flakes which allow to produce high quality effect pigments.

The DE 199 07 313 A1 discloses the use of shiny pigments coated with several layers in cosmetics. DE 199 07 313 A1 does not disclose pearlescent pigments based on glass flakes are mentioned.

DE 10 2005 029 647 A1 discloses cosmetic formulations providing a protection against infrared rays. The protection is mainly achieved by pearlescent pigments, which partly reflect infrared radiation. The pearlescent pigments are based on all kinds of common substrates: synthetic or natural mica, $SiO_2$-platelets, $Al_2O_3$-platelets, glass flakes or polymer flakes.

Pearlescent pigments based on $Al_2O_3$-platelets, however, are available only in sizes below about 30 μm. Manufactures of pearlescent pigments for the cosmetic market, however, want to offer a product program of various sizes based on a single source of substrate. $SiO_2$-flakes are expensive to produce and quite difficult to be produced in constant quality. Furthermore they exhibit extremely high colourflops which are not always demanded. Glass flakes would be the best choice as artificial substrates for effect pigments, especially for pearlescent pigments, because they can be produced reproducibly at fairly low costs and are achievable in various sizes and thicknesses.

In cosmetic formulations there is still a demand for glass flake-based pearlescent pigments with improved skin feeling and higher gloss properties.

SUMMARY:

Therefore, it is an object of this invention to provide a cosmetic formulation containing pearlescent pigments with better skin feeling and higher gloss properties than hitherto used pearlescent pigments based on glass flakes.

The object underlying the present invention is solved by providing a cosmetic composition comprising an effect pigment based on a glass flake as a substrate with a coating, said coating comprising at least one layer of at least one high refractive material, said material having a refractive index of at least 1.8, and/or a semitransparent metal coating wherein said glass flakes comprise the following composition:

65-75 wt.-% silicon oxide, preferably $SiO_2$
2-9 wt.-% aluminium oxide, preferably $Al_2O_3$
0.0-5 wt.-% calcium oxide, preferably CaO
5-12 wt.-% sodium oxide, preferably $Na_2O$
8-15 wt.-% boron oxide, preferably $B_2O_3$
0.1-5 wt.-% titanium oxide, preferably $TiO_2$
0.0-5 wt.-% zirconium oxide, preferably $ZrO_2$
based on the weight of said glass flakes.

For handling effect pigments, for example, during the production of the cosmetic formulations it is desirable that the effect pigments are mechanically stable in order to avoid, e.g., delamination of coated layers.

Surprisingly, the strength of adhesion of the applied layers can be further improved by incorporation of small amounts of titanium oxide, preferably titanium dioxide, into glass compositions used in the production of effect pigments of the present invention. The at least one layer of high refractive material and/or at least one layer of semitransparent metallic material of the effect pigments used in the cosmetic composition of the present invention is firmly adhered to the glass flake containing titanium oxide, preferably titanium dioxide. The content of titanium oxide is preferably in a range of 0.5 to 2.5 wt.-% and more preferably in the range of 1 to 2 wt.-%, based on the weight of said glass flake.

A content above 5 wt.-% of $TiO_2$ does not further improve the strength of adhesion of subsequent layers in the glass composition as specified in claim 1. Therefore, further increasing the content of titanium oxide unnecessarily increases the costs and reduces the difference in the index of refraction of the glass substrate and the at least one high refractive index layer and/or semitransparent metallic layer. The larger the difference of the refractive index of the glass flake substrate and of the subsequent layer(s) of high refractive material and/or semitransparent metallic material the stronger are the interference effects of the obtained pearlescent pigments. A stronger interference effect can lead, for example, to a stronger colour flop of the pearlescent pigment.

DETAILED DESCRIPTION

Preferably, said glass composition of the effect pigment comprises a content of titanium oxide of at least 0.5 wt.-%, preferably at least 1 wt.-% of $TiO_2$, based on the weight of said glass flake.

Surprisingly, the pearlescent effect pigments used in the present invention do combine the features of a superior mechanical stability and reduced hardness. It is assumed that the reduced hardness is associated with the low contents of aluminium oxide and calcium oxide in the glass composition, respectively.

Most surprisingly, the pearlescent pigments of the present invention have also a softer skin feeling, which renders these pearlescent pigments particular useful as an ingredient for cosmetics.

Preferably, the said glass composition comprises a content of 67-73 wt.-% of silicon oxide, preferably $SiO_2$, based on the weight of said glass flake.

Preferably, the said glass composition comprises a content of 4-7 wt.-% of aluminium oxide, preferably $Al_2O_3$, based on the weight of said glass flake.

Preferably, the said glass composition comprises a content of 0.5-2.5 wt.-% and more preferably 1-2.5 wt.-% of calcium oxide, preferably CaO, based on the weight of said glass flake.

Preferably, the said glass composition comprises a content of 8.5-14 wt.-% of boron oxide, preferably $B_2O_3$, more preferably of 9-13 wt.-% of boron oxide, preferably $B_2O_3$, based on the weight of said glass flake.

Preferably, the said glass composition comprises a content of zirconium oxide, preferably $ZrO_2$, of 0.05 to 3.0 wt.-%, preferably of 0.1 to 1.5 wt.-%, based on the weight of said glass flake.

Preferably, the said glass composition comprises a content of sodium oxide, preferably $Na_2O$, of 6 to 11 wt.-% based on the weight of said glass flake.

In a further embodiment of the said glass composition comprises the following further components:

0 to 6 wt.-%, preferably 1 to 4 wt.-%, potassium oxide and/or lithium oxide, preferably $K_2O$ and $Li_2O$, respectively, and/or 0 to 6 wt.-%, preferably 1.0 to 4.0 wt.-% magnesium oxide, preferably MgO.

The sum of all components of the above glass compositions, including those components not mentioned above do amount in total each to 100 wt.-%.

The glass flake composition used as a substrate for the effect pigments used in the cosmetic composition of the present invention is not a C-glass which is characterised by its superior corrosion resistance. The glass flake composition used as a substrate for the effect pigments used in the cosmetic composition of the present invention is less corrosion resistant than C-glass. Especially in distilled water and in acidic environments the glass flake composition used as substrate in the present invention proved to be less corrosion resistant. In view of EP 0 912 640 B1 teaching that only C-glass flakes can be used for producing pearlescent pigments of high quality it is therefore very surprising that pearlescent pigments of very high optical qualities are obtained with such a glass flake composition having a low corrosion resistance.

Coating of glass flakes with high refractive index materials such as $TiO_2$ is usually done in aqueous media at ph 1-2 and at elevated temperatures. One would expect that using glass flakes of low corrosion stability under these conditions would lead to a very strong roughening of surface of the glass flake due to dissolution of ions. This would finally lead to a low quality of pearlescent pigments with respect to optical properties like gloss and/or colour flops.

Surprisingly, the present inventors found out that pearlescent pigments with higher gloss can be produced by a glass flake composition of this invention compared to C-glass.

Without being bound to theory it is believed that this unexpected effect is due to a much finer particle size of the coating of the high refractive index material. High refractive index materials, especially metal oxides are well known to be coated in form of oxide grains. Larger grains in the range of more than 50 nm, e.g. more than 75 nm and e.g. more than 100 nm can lead to significant scattering which reduces the gloss of such pearlescent pigments.

It turned surprisingly out that the oxide grains formed on the surface of the glass flakes used in the present invention are very small or fine resulting in a very smooth coating with metal oxide layer(s), such as, e.g., a coating of titanium oxide and/or iron oxide, what in turn results in superior optic properties of the pearlescent pigments of the present invention.

It is currently not understood why glass flakes of the composition of this invention lead to such an effect.

Without being bound to a theory it is currently believed that the lower corrosion resistance compared to the commonly used C-glass of the inventive glassflakes is the reason for this above-mentioned effect. The coating of the high refractive index materials such as $TiO_2$ occurs at low pH-values of about 1-2. Some metals of the glass flake may be dissolved under these conditions leading to flaws and enhancing the probability to form metal hydroxide and especially silanol functions on the surface of the glass flake. These hydroxide groups can function as excellent binding sites and thus nucleation centers for the precipitating metal oxide precursors. Thus the metal oxide binds better to the glass flakes surface which is very important in the very early stages of the precipitation process. Consequently, the metal oxide can be precipitated in a much finer grain size. Such finer grain sizes of the high refractive index metal oxide in turn lead to lower scattering and thus enhanced gloss and optical properties.

In a further preferred embodiment of the invention the said glass composition has a softening point below 800° C. Such a glass can be produced with less energy costs and hence less total costs. Pursuant to a preferred embodiment of the invention the softening point of the glass composition is in a range of 600° C. to less than 800° C., preferably from 620° C. to 750° C. and further preferred from 650° C. to 700° C.

The inventors of the present invention have realised that the composition of the surface of a glass substrate can have a significant impact on the optical properties of pearlescent pigments using glass flakes as a substrate, in particular if these glass flakes are coated with several layers. Using the effect pigments on the basis of these glass flake substrates in a cosmetic composition enables a superior decorative effect on a substrate, such as hair, skin, fingernail, toenail, etc.

Preferably, the glass flakes containing titanium oxide as a substrate for the effect pigments used in the cosmetic composition of the present invention have a refractive index of less than 1.8. Most preferably the refractive index of the glass flakes is within a range of 1.40 to 1.80, more preferred in a range of 1.45 to 1.7 and mostly preferred in a range of 1.50 to 1.60.

Pursuant to another preferred embodiment of the invention, the difference between the refractive index of the glass flake containing titanium oxide and the subsequently applied layer or layers of high refractive material(s) is at least 0.6, more preferably at least 0.8 and further preferred at least 1.0. According to another preferred embodiment, the difference of the refractive index between the glass flakes substrate and the subsequently applied layer(s) of high refractive material(s) is in a range of 0.9 to 1.3.

When applying titanium dioxide, having a refractive index of 2.7, as a high refractive material on a glass flake having a content of titanium dioxide as specified in claim 1, it is possible to obtain a difference of refractive index between said glass flake and the subsequently titanium dioxide layer in a range of 0.9 up to 1.3, preferably of 1.0 to 1.2.

According to an embodiment of the invention the effect pigments, used in the cosmetic composition, comprise one or more layers of high refractive material(s), such as metal oxide(s) or metal sulfide(s), which can be coated directly on each other.

The high refractive materials, for example metal oxide(s), metal sulfide(s), have preferably a refractive index of at least 2.0, further preferred of at least 2.2. Pursuant to another embodiment of the invention the refractive index of the high refractive material(s) is at least 2.3. The refractive index can be up to 2.7, 2.9 or 3.5.

For example, a layer of $TiO_2$ can be directly applied on the surface of the glass flakes containing $TiO_2$, followed by a subsequent layer of $Fe_2O_3$, or vice versa. It is, of course, also possible to directly apply a layer composed of a mixture of various high refractive materials such as metal sulfides or metal oxides. A particular useful mixture of metal oxides is a mixture of $TiO_2$ and $Fe_2O_3$.

According to another embodiment of the invention the layer of high refractive material, e.g. metal oxide and/or metal sulfide, directly applied to the surface of the glass flakes can be doped with tin oxide and/or aluminium oxide. Such doping with tin oxide and/or aluminium oxide may also increase the adhesion between the high refractive material layer on the surface of the glass flakes. When applying an intermediate layer of aluminium oxide or when using aluminium oxide as a doping agent, it is preferred to use aluminium oxide in the boehmite modification.

According to a preferred embodiment of the invention the high refractive material is selected from the group consisting of metal chalcogenides, particularly metal oxides, metal suboxides and metal sulfides, metal oxyhalides, metal nitrides, metal carbides, semitransparent metals and mixtures thereof.

Preferably said high refractive material is preferably selected from the group of metal oxides consisting of titanium dioxide, iron oxides, e.g. hematite, magnetite, goethite, chromium oxide, copper oxide, zinc oxide, tin oxide, vanadium oxide, nickel oxide, antimony oxide, lead oxide, silver oxide, molybdenum oxide, tungsten oxide, zirconium oxide, suboxides and mixtures thereof. Preferred high refractive materials are titanium dioxide and/or iron oxides.

Pursuant to another embodiment of the invention said high refractive material is selected from the group of metal sulfides consisting of titanium sulfide, iron sulfide, chromium sulfide, copper sulfide, zinc sulfide, tin sulfide, nickel sulfide, vanadium sulfide, cobalt sulfide, antimony sulfide, lead sulfide, silver sulfide, lanthanum sulfides, preferably cerium sulphide, molybdenum sulfide, tungsten sulfide, zirconium sulfide, subsulfides and mixtures thereof.

Particularly preferred effect pigments used preferably in the cosmetic composition of the present invention are glass flakes comprised a composition according to claim 1 and comprising or consisting of coatings with the specified high refractive material:
glass flake+$TiO_2$ layer with $TiO_2$ being in the rutile modification
glass flake+$TiO_2$ layer with $TiO_2$ being in the anatase modification
glass flake+$Fe_2O_3$ layer
glass flake+$TiO_2$/$Fe_2O_3$ layer with $TiO_2$ being in the rutile modification
glass flake+$TiO_2$/$Fe_2O_3$ layer with $TiO_2$ being in the anatase modification
glass flake+$TiO_2$ layer+$Fe_2O_3$ layer with $TiO_2$ being in the rutile modification
glass flake+$TiO_2$ layer+$Fe_2O_3$ layer with $TiO_2$ being in the anatase modification
glass flake+$Fe_2O_3$ layer+$TiO_2$ layer with $TiO_2$ being in the rutile modification
glass flake+$Fe_2O_3$ layer+$TiO_2$ layer with $TiO_2$ being in the anatase modification
glass flake+$TiFe_2O_5$ layer
glass flake+$Cr_2O_3$ layer
glass flake+$ZrO_2$ layer
glass flake+Sn (Sb)$O_2$ layer
glass flake+BiOCl layer
glass flake+$Al_2O_3$ layer+$TiO_2$ layer with $TiO_2$ being in the rutile modification
glass flake+$SnO_2$ layer+$TiO_2$ layer with $TiO_2$ being in the rutile modification
glass flake+$Al_2O_3$/$TiO_2$ layer with $TiO_2$ being in the rutile modification
glass flake+$SnO_2$/$TiO_2$ layer with $TiO_2$ being in the rutile modification
glass flake+$Ce_2S_3$ layer
glass flake+$MOS_2$ layer The $TiO_2$-coating can exist in the rutile or anatase modification, preferably rutile. In order to apply the titanium dioxide coating in the rutile modification, a precoat consisting of $SnO_2$, $Al_2O_3$ or $Fe_2O_3$ is first applied followed by a subsequent layer of titanium dioxide. The thickness of the precoat $SnO_2$ or $Fe_2O_3$ is preferably <10 nm and most preferably <5 nm.

In addition, layers from $Fe_2O_3$ or $Fe_2O_3$/$TiO_2$-layers and $Cr_2O_3$ are especially preferred as these layers are capable to produce for example skin colour tones, which satisfy decorative demands (bifunctional make-up). Therefore, cosmetic compositions comprising the aforementioned effect pigments are particularly preferred.

Pursuant to another embodiment of the invention the glass flakes can be coated with a semitransparent metal to provide pearlescent effect pigments for use in the cosmetic composition. This said semitransparent metal is selected from the group consisting of aluminium, chromium, silver, gold, copper, titanium, nickel, zinc and mixtures and alloys of these metals. The term "semitransparent" means a transparency of 10 to 90%, preferably of 30 to 70% and most preferably of 40 to 60%, respectively. Thin metal layers of these transparencies are capable to give rise to interference effects with the underlying glass flake substrate. The thickness of these semitransparent metal layers is preferably in a range of between 0.2 nm and 20 nm, preferably between 3 nm and 15 nm.

The semitransparent metal can be coated directly on the glass flake. In this case an interference effect pigment is obtained with a rather metallic appearance.

In another embodiment of the invention this interference pigment, contained in the cosmetic composition of the present invention, can be further coated with high refractive materials.

In another embodiment of the invention the semitransparent metal layer is coated onto a first layer of high refractive index materials.

Particularly preferred effect pigments of the present invention are glass flakes comprised a composition according to claim 1 and comprising or consisting of coatings with the specified semitransparent metals:
glass flake+Al layer
glass flake+Ag layer
glass flake+$TiO_2$ layer+Al layer
glass flake+$TiO_2$ layer+Ag layer
glass flake+$Fe_2O_3$ layer+Al layer
glass flake+$Fe_2O_3$ layer+Ag layer The metal layers can be deposited by known methods such as CVD-, PVD-methods or by electroless plating.

In a further preferred embodiment the pearlescent pigments comprise at least one layer of low refractive and at least one layer of high refractive index material.

The low refractive index material refers to materials with a refractive index of <1.8, preferably of <1.7.

Pursuant to another embodiment of the invention the effect pigment comprises a plurality of layers of low refractive and high refractive materials, such as metal oxide(s) and/or metal sulfide(s). According to another embodiment of the invention said layers of low refractive and high refractive materials are alternately arranged on each other.

Especially preferred are alternating layers of high refractive materials with low refractive materials. Such pearlescent pigments are known to exhibit especially strong interference colours. Pearlescent pigments with such alternating layers are, for example, known from the DE 196 18 566 A1, DE 196 38 708, JP 7-246366, EP 1 025 168 A1 or EP 0 753 545 A2.

The at least one layer of low refractive material is selected from the group consisting of low refractive metal oxides, particularly of silica, silica hydrate, silicon oxide hydroxide, silicon oxide hydroxide hydrate, alumina, alumina hydrate, aluminium oxide hydroxide, aluminium oxide hydroxide hydrate, boron oxide, boron hydroxide, magnesium fluoride, magnesium silicate and mixtures thereof.

Examples of suitable metal oxides having a refractive index of more than 1.8 are $TiO_2$, $Fe_2O_3$, $TiFe_2O_5$, Ti-suboxides, $Fe_3O_4$, $Cr_2O_3$, $ZrO_2$, $ZnO$, $SnO_2$, $Sn(Sb)O_2$ or mixtures thereof.

The $TiO_2$ layer can be in the rutile or anatase modification, preferably the $TiO_2$ layer is rutile. Especially preferred are glass flakes coated with $TiO_2$ and/or $Fe_2O_3$.

Pursuant to a preferred embodiment the glass flakes are coated preferably with one or more layers of metal oxide selected preferably from the group consisting of $TiO_2$, $Fe_2O_3$ and mixtures thereof.

Depending on the thickness of the layer(s) of $TiO_2$ and/or $Fe_2O_3$ and the thickness of the low refractive index layer a wide range of colour effects can be produced.

Pursuant to another embodiment of the invention, the one or more metal oxide layers of titanium dioxide is/are in the rutile modification. Rutile has a higher index of refraction compared to anatase and is less photoactive.

If the effect pigments used in the present invention containing $TiO_2$ in the high refractive index coating are used a subsequent protection coating, e.g., a layer of silicon oxide and/or cerium oxide is preferably applied to suppress the photoactivity, if any. The protection coating can be composed of a first layer of silicon oxide and a second layer of cerium oxide and vice versa, wherein the latter arrangement of layers is particularly preferred.

In a further preferred embodiment the pearlescent pigments are so-called multilayer pigments which comprise the following coatings:

(A) a coating with a refractive index of n>1.8 and an average thickness of 50-350 nm,
(B) a coating with a refractive index of n<1.8 and an average thickness of 50-500 nm,
(C) a coating with a refractive index of n>1.8 and an average thickness of 20-350 nm.

The thickness of the coatings (A) (B) or (C) can be equal or may differ from each other. Preferably the thickness of the layers (A) and (C) are in the range of 20-350 nm, more preferred 50-250 nm and especially preferred 70-150 nm.

The coating (B) has preferably a thickness of 50-500 nm, more preferred of 100-200 nm and especially preferred 130-180 nm, and is preferably $B_2O_3$, $SiO_2$ and/or $Al_2O_3$.

The thickness of the coatings (A) und (C) can be equal or may differ from each other. In a most preferable embodiment the coatings (A) und (C) are colourless coatings, especially $TiO_2$-coatings. The $TiO_2$-coating can exist in the rutile or anatase modification, preferably rutile. In order to apply the titanium dioxide coating in the rutile modification a precoat consisting of $SnO_2$, $Al_2O_3$ or $Fe_2O_3$ can be applied first followed by a subsequent layer of titanium dioxide. The thickness of the precoat $SnO_2$ or $Fe_2O_3$ is preferably <10 nm and most preferably <5 nm.

Particularly preferred multi layer pearlescent pigments used in the cosmetic composition of the present invention are glass flakes comprised of a composition recited claim 1 and comprising or consisting of coatings with the specified high and low refractive materials:

Glass-flake+$TiO_2$+$SiO_2$+$TiO_2$
Glass-flake+$Fe_2O_3$+$SiO_2$+$TiO_2$
Glass-flake+$TiO_2$+$SiO_2$+$TiO_2$/$Fe_2O_3$
Glass-flake+$TiO_2$/$Fe_2O_3$+$SiO_2$+$TiO_2$/$Fe_2O_3$
Glass-flake+$TiO_2$/$Fe_2O_3$+$SiO_2$+$TiO_2$
Glass-flake+$TiO_2$/$Fe_2O_3$+$SiO_2$+$Fe_2O_3$
Glass-flake+$Fe_2O_3$+$SiO_2$+$TiO_2$/$Fe_2O_3$
Glass-flake+$SiO_2$+$TiO_2$+$SiO_2$+$TiO_2$
Glass-flake+$SiO_2$+$Fe_2O_3$+$SiO_2$+$TiO_2$
Glass-flake+$SiO_2$+$TiO_2$+$SiO_2$+$TiO_2$/$Fe_2O_3$
Glass-flake+$SiO_2$+$TiO_2$/$Fe_2O_3$+$SiO_2$+$TiO_2$/$Fe_2O_3$
Glass-flake+$SiO_2$+$TiO_2$/$Fe_2O_3$+$SiO_2$+$TiO_2$
Glass-flake+$SiO_2$+$TiO_2$/$Fe_2O_3$+$SiO_2$+$Fe_2O_3$
Glass-flake+$SiO_2$+$Fe_2O_3$+$SiO_2$+$TiO_2$/$Fe_2O_3$ Glass flakes used in the present invention have a thickness preferably in the range of 0.05 to 10 μm, further preferably of 0.1 μm to 2.0 μm. Pursuant to another embodiment of the invention the thickness of the glass flakes is in a range of 0.05 μm to 1.0 μm, more preferably of 0.1 μm to 0.45 μm.

Very thin glass flakes are preferred, because very brilliant colour effects can be achieved with them. Preferably the glass flakes are produced by methods disclosed in the WO 2004/056716 A1, WO 2005/063637 A1 and the EP 0 289240 A1, which are enclosed by reference therein.

The average particle size of the glass flakes used as a substrate for the effect pigments used in the cosmetic composition in the present invention is preferably in the range of 1 to 1000 μm, more preferably in the range of 5 to 500 μm. Preferred glass flakes have an average particle size in the range of 10 to 200 μm.

The aspect ratio of the glass flakes used as a substrate for the effect pigments used in the cosmetic composition is preferably in the range of 20 to 10,000, preferably in the range of 200 to 3,000. Pursuant to another embodiment of the invention, the aspect ratio is in the range of 300 to 1,500.

If the high refractive index material comprises $TiO_2$ either alone or in admixture with another compound, such as $TiO_2$/$Fe_2O_3$, a subsequent layer of $SiO_2$ and/or cerium oxide is preferably applied if the photocatalytic activity of the pearlescent pigment is to be isolated from the surrounding. Such protective coatings are described in the DE 10 2004 041 592 A1 and the DE 10 2004 041 586 A1, which are incorporated herein by reference.

It is also possible to additionally include colouring matters such as dyes, colourants, etc. into the layer(s) of high refractive material, such as a metal oxide layer, or a layer of low refractive material, such as a layer of $SiO_2$ or $Al_2O_3$, or as a separate layer onto the surface of the coating containing the at least one layer of high refractive material. Such colouring matter can be, for example, carmine, Prussian blue (ferric cyanoferrate (II)), carbon black, copper phthalocyanines, diketo pyrrolo pyrrolidones, chinacridones, indolines, isoindolines, azopigments, anthrachinones, FD&C dyes or FD&C lakes.

The surface of the effect pigments used in the present invention may also be organic-chemically modified. Such an organic-chemical surface modification may render the effect pigments a leafing behaviour or a non-leafing behaviour.

Pursuant to a preferred embodiment the glass flakes are coated with at least one layer of a high refractive material and/or a semitransparent metal by wet chemical coating, physical vapour deposition, chemical vapour deposition, or electroless plating.

The glass flakes can be coated in the same way as e.g. mica based pearlescent pigments. Coatings with a metal oxide may be accomplished by any known methods, such as hydrolysis of a metal salt by heating or alkali, which deposits hydrated metal oxide, optionally followed by calcination.

In general, the procedure can involve dispersing of the glass flakes in a suitable solvent, for example organic solvent or water or a water/organic solvent mixture, and combining that dispersion with a precursor which forms a hydrous metal oxide film coating on the flakes. The precursor can be metal salts hydrolysed and subsequently deposited on the glass flake surface.

After the glass flakes are dispersed in water and placed in an appropriate vessel, the appropriate metal salts are added. The pH of the resulting dispersion is maintained at an appropriate level during the addition of the metal salts by simultaneous feeding a suitable base, for example sodium hydroxide, to cause precipitation of the hydrous metal dioxide on the glass flakes. An aqueous acid, for example hydrochloric acid, can be used for adjusting the pH. The coated platelets can, if desired, be washed and dried before being calcined to the final pigment. Appropriate procedures are described in detail in U.S. Pat. No. 5,433,779 and in the German Patents 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 3211 602 and 32 53 017 which are incorporated herewith by reference.

Alternatively, alkoxy metal compounds can be dispersed in an organic solvent. The hydrolysis of said alkoxy metal compounds can be started by adding water, for example in an amount of about 1 to 20 wt.-%, preferably 5 to 10 wt.-%, based on the weight of the organic solvent. After hydrolysis of the alkoxy metal compounds, a metal oxide layer is formed on the surface of the glass flakes. As organic solvent preferably alcohols such as ethanol, n-propanol or isopropanol and mixtures thereof can be used.

The effect pigments obtained by wet chemically coating are characterized in that one or more homogeneous layers are enrobing the glass flakes.

The effect pigments used in the cosmetic preparation of the present invention can also be prepared by gas phase decomposition of volatile metal compounds (CVD, PVD) or electroless plating by procedures known in the art.

The cosmetic compositions of this invention can be used in cosmetic formulations in the decorative cosmetics or personal care applications.

The cosmetic composition of the present invention can be prepared by working in the effect pigments into a cosmetic pre-formulation or formulation, for example, by mixing using a stirrer.

The cosmetic compositions according to the invention may also comprise further dyes and coloured pigments. The dyes and coloured pigments can be selected from the corresponding positive list in the German Cosmetics Regulation or the EU list of cosmetic colorants. In most cases, they are identical with the dyes approved for foods. Advantageous coloured pigments are, for example, titanium dioxide, mica, iron oxides (for example $Fe_2O_3$, $Fe_3O_4$, FeO(OH)) and or tin oxide. Advantageous dyes are, for example, carmine, Berlin Blue, Chromium Oxide Green, Ultramarine Blue and or Manganese Violet. It is particularly advantageous to select the dyes and or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Ch oro-4'-nitro-1'-phenylazo)-2-hydroxynaphthalene | 12085 | red |
| Pigment Red 3 | 12120 | red |
| Ceres Red; Sudan Red; Fat Red G | 12150 | red |
| Pigment Red 112 | 12370 | red |
| Pigment Red 7 | 12420 | red |
| Pigment Brawn 1 | 12480 | brown |
| N-(5-chloro-2,4-dimethoxyphenyl)-4-[[5-[diethylamino)-sulfonyl]-2-methoxyphenyl]azo]-3-hydroxynaphthalene-2-carboxamide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxy-azobenzene-4'-sulfonic acid | 14270 | orange |
| 2-(2,4-Dimethylphenylazo-5-sulfonyl)-1-hydroxynaphthalene-4-sulfonic acid | 14700 | red |
| 2-(4-Sulfo-1-naphthylazo)-1-aaphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonyl-4-chloro-5-carboxy-1-phenylazo)-2-hydroxynaphthalene | 15525 | red |
| 1-(3-Methylphenylazo-4-sulfonyl)-2-hydroxynaphthalene | 15580 | red |
| (4',(8') Sulfonyl)-2-hydroxynaphthalene | 15620 | red |
| 2-Hydroxy-1,2'-azonaphthalene-1'-sulfonic acid | 15630 | red |
| 3-Hydroxy-4 phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxy-naphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-sulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid ellow 121 | 18690 | yellow |
| Acid Red 180 | 18736 | red |
| Acid 'Yellow 11 | 18820 | yellow |
| Acid Yellow 1 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2",4"-dimethyl)bisphenylazo)-1,3-Dihydroxy-benzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4"-Sulfo-1"-phenylazo-7-sulfo-1'-naphthylazo]-1-hydroxy-7-aminonaphthalene-3,6-disulfonic acid | 27755 | black |
| 4-[4"-Sulfo-1"-phenylazo)-7'-sulfo-1'-naphlhylazol-1-hydroxy-8-acetylaminonaphthalene-3,5-disulfcnic acid | 28440 | black |
| Direct Orange 34, 39, 44, 46, 60 | 40215 | orange |
| Food Yellow | 40800 | orange |
| trans-13-Apo-8'-carotene aldehyde ($C_{30}$) | 40820 | orange |
| trans-Apo-8'-carolinic acid ($C_{30}$) ethyl ester | 40850 | orange |
| Canthaxanthine | 40850 | orange |

-continued

| Chemical or other name | CIN | Colour |
|---|---|---|
| Acid Blue 1 | 42045 | blue |
| 2,4-Disulfo-5-hydroxy-4'-4''-bis(diethylamino)triphenvlcarbinol | 42051 | blue |
| 4-[(-4-N-Ethyl-p-sulfobenzylamino)-phenyl-(4-hydroxy-2-sulfophenyl) (methylene)-1-(N-ethyl1-N-p-sulfobenzyl-2,5-cyclohexadienimine] | 42053 | green |
| Acid Blue 7 | 42080 | blue |
| (N-Ethyl-p-sulfobenzylamino)phenyl-(2-sulfophenyl)methylene-(N-ethyl-N-p-sulfobenzyl)-$\Delta^{2,5}$-cyclohexadienimine | 42090 | blue |
| Acid Green 9 | 42100 | green |
| Diethyldisulfobenzyldi-4-amino-2-chlorodi-2-methylfuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4'-(N-diethyl)-amino-2-methyl-N-ethyl-N-m-sulfobenzylfuchsonimmonium | 42735 | blue |
| 4' (N Dimethyl)amino 4'' (N phenyl)aminonaphtho-N-dimethylfuchsonimnionium | 44045 | blue |
| 2 Hydroxy 3,6 disulfo 4,4' bisdimethylamino-naphthofuchsonimmonium | 44090 | green |
| Acid Red 52 | 45100 | red |

It may furthermore be favourable to select, as dye, one or more substances from the following group: 2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-napthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-2-(4-sulfophenyl)-5-hydroxypyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium is salt of indigodisulfonic acid, red and black iron oxide (CIN: 77 491 (red) and 77 499 (black)), iron oxide hydrate (CN: 77492), manganese ammonium diphosphate and titanium dioxide.

Also advantageous are oil-soluble natural dyes, such as, for example, paprika extract, n-carotene or cochineal.

Furthermore, the cosmetic composition of the present invention may include inorganic or organic pigments. Preferably, organic pigments are selected from the group consisting of chinacridones, xanthenes, indigos, cyanines, antocyanes, indanthrenes, isoindolines, monoazo-, bisazo-, trisazopigments, chinolphtalones, anthrachinones, phthalocyanines, carotinoides or mixtures thereof.

Preferred inorganic pigments are selected from the group consisting of $TiO_2$, coloured $SiO_2$, $CaSO_4$, iron oxides, chromium oxides, soot or their mixtures.

The cosmetic composition of the present invention comprise the effect pigments based on the new glass composition described above and dyes or pigments in amounts of 0.5-50 wt.-%; preferably of 1-30 wt.-%; and further preferably of 3-15 wt.-%; based on the total weight of the cosmetic composition, depending on the field of application.

The weight-ratio of the effect pigment to dyes or pigments is preferably 30:1 to 1:10 wt., preferably 20:1 to 1:5, and most preferably 5:1 to 1:5, depending on the field of application.

Also advantageous for the purposes of the present invention are gel creams comprising other pearlescent pigments. Particular preference is given to the types of pearlescent pigment listed below:
1. Natural pearlescent pigments, such as, for example,
   a) "pearl essence" (guanine hypoxanthine mixed crystals from fish scales) and
   b) "mother-of-pearl" (ground mussel shells)
2. Monocrystalline pearlescent pigments, such as, for example, bismuth oxychloride (BiOCl)

The effect pigments of the present invention can also be used in the cosmetic preparation in admixture with other coloured or black pearlescent pigments based on metal oxide coated mica, $TiO_2$ flakes, $SiO_2$ flakes or $Al_2O_3$ flakes and coated or uncoated metal pigments, cholesteric flakes, BiOCl pigments, platelet shaped iron oxides, or graphite flakes.

The cosmetic composition of the present invention can be of any type and be used, for example, for decorative effects on the skin, hair, eyelids, fingernails or toenails, etc. Furthermore, the cosmetic composition or formulation of the present invention may also be combined with other active agents, e.g., pharmaceutically active agents such as dermatologically active agents.

Cosmetic compositions according to the invention or compositions to be used in accordance with the invention may also comprise one or more insect repellents. According to a preferred embodiment of the invention, the at least one repellent is selected from N,N-diethyl-3-methylbenzamide, ethyl 3-(acetylbutylamino)propionate, dimethyl phthalate, butopyronoxyl, 2,3,4,5-bis(2-butylene)tetrahydro-2-furaldehyde, N,N-diethylcaprylamide, N,N-diethylbenzamide, o-chloro-N,N-diethylbenzamide, dimethyl carbate, di-n-propyl isocinchomcronate, 2-ethylhexane-1,3-diol, N-octylbicycloheptenedicarboximide, piperonyl butoxide, 1-(2-methylpropoxycarbonyl)-2-(hydroxyethyl)piperidine, or mixtures thereof, where it is particularly preferably selected from N,N-diethyl-3-methylbenzamide, ethyl 3-(acetylbutylamino)propionate, 1-(2-methylpropoxycarbonyl)-2-(hydroxyethyl)piperidine, octanoic acid, decanoic acid, pyrethrins, pyrethroids, methyl nonyl ketone (undecan-2-one), cycloalkanecarboxylic acids, permethrin and (R)-p-menthal, 8-diol, as well as effective derivatives of the said active ingredients which are known from the literature, or mixtures thereof.

In a preferred embodiment of the present invention, the cosmetic composition may additionally comprise active agents protecting human or animal body cells against oxidative stress, in particular for reducing skin ageing, such as one or more antioxidants.

There are many proven substances which can be used as antioxidants in a cosmetic composition of the present invention, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurrylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B1), riboflavin (vitamin B), nicotinamide, vitamin C (ascorbic acid), vitamin D, ergocalciferol (vitamin D2), vitamin E, DL-α-tocopherol, tocopherol P acetate, tocopherol hydrogensuccinate, vitamin K1, esculin (vitamin P active ingredient), thiamine (vitamin B1), nicotinic acid (niacin), pyridoxine, pyridoxal, pyridoxamine (vitamin BO), pantothenic acid, biotin, folic acid and cobalamine (vitamin B12), particularly preferably vitamin A palmitate, vitamin C and derivatives thereof, DL-α-tocopherol, tocopherol P acetate, nicotinic acid, pantothenic acid and biotin.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; *Current Topics in Biophysics* 2000, 24 (2), 101-108, are concerned with effects of the substitution pattern of mono- and dihydroxyflavones. It is observed therein that dihydroxyflavones containing an OH group adjacent to the keto function or OH groups in the 3,4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N.J. Miller, G. Paganga, *Trends in Plant Science* 1997, 2 (4), 152-159). K. Lemanska, H. Szymusiak, B. Tyrakowska, R. Zielinski, A. E. M. F. Sollers, I. M. C. M. Rietjens; Free Radical Biology&Medicine 2001, 31 (7), 869-881, have investigated the pH dependence of the antioxidant action of hydroxyflavones. Quercetin exhibits the greatest activity amongst the structures investigated over the entire pH range.

Cosmetic compositions which are particularly preferred in accordance with the invention are those which convey sun protection and preferably also comprise UV filter(s) and/or UV absorber(s).

In principle, all UV filters are suitable for use in the cosmetic composition in accordance with the invention. Particular preference is given to UV filters whose physiological acceptability has already been demonstrated. Both for UVA and UVB filters, there are many proven substances which are known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)$_m$-ethyl]-benzyl}acrylamide (for example Mexoryl® SW), N,N,N-trimethyl-4-(2-oxoborn-3-ylidenemethyl) anilinium methylsulfate (for example Mexoryl® SIC) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyldibenzoyl-methane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292), isopentyl 4-methoxycinnamate, for example as a mixture of the isomers (for example Neo Heliopan® IE 1000), salicylate derivatives, such as 2-ethylhexyl salicylate (for example Eusolex® OS), 4-isopropylbenzyl salicylate (for example Megasol®) or 3,3,5-trimethylcyclohexyl-salicylate (for example Eusolex® HMS), 4-aminobenzoic acid and derivatives, such as 4-aminobenzoic acid, 2-ethylhexyl 4-(dimethylamino)benzoate (for example Eusolex® 6007) or ethoxylated ethyl 4-aminobenzoate (for example Uvinul® P25), phenylbenzimidazolesulfonic acids, such as 2-phenylbenzimidazole-5-sulfonic acid and the potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as 2-ethylhexyl 2-cyano-3,3-diphenylacrylate (for example Eusolexe OCR), 3,3'-(1,4-phenylenedimethylene)bis(7,7-dimethyl-2-oxobicyclo [2.2.1]-hept-1-ylmethanesulfonic acid and salts thereof (for example Mexoryl® SX), 2,4,6-trianilino-(p-carbo-2'-ethylhexyl-1'-oxy)-1,3,5-triazine (for example Uvinul® T 150) and hexyl 2-(4-diethylamino-2-hydroxybenzoyl-) benzoate (for example Uvinul® UVA Plus, BASF).

The compounds mentioned in the list should only be regarded as examples. It is of course also possible to use other UV filters.

These organic UV filters are preferably incorporated into the formulations in an amount of from 0.5 to 10 percent by weight, preferably 1-8%.

Further suitable organic UV filters are, for example, 2-(2H-benzotriaxol-2-yl)-4-methyl-6-(2-methyl-3-(1,3,3,3-tetra methyl-1-(trimethylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl-)diimino]bis(benzoate) (for example Uvasorb® HEB), α-(trimethylsilyl)-ω-[trimethylsilyl)oxy]poly[oxy(dimethyl [and approx. 6% of methyl[2-[p-[2,2-bis(ethoxycarbonyl] vinyl]phenoxy]-1-methylenethyl]

and approx. 1.5% of methyl[3-[p-[2,2-bis(ethoxycarbonyl) vinyl)phenoxy)propenyl) and 0.1 to 0.4% of (methylhydrogen]silyiene]] (n ≈60) (CAS No. 207 574 74-1), 2,2'-methylenebis(6-(2H-benxotriazol-2-yl)-4-(1,1,3,3-tetramethylbutyl)phenol) (CAS No. 103 597-45-1), 2,2'-(1,4-phenylene)bis(1H-benximidaxole-4,6-disulfonic acid, monosodium salt) (CAS No. 180 898-37-7) and 2,4-bis{[4-(2-ethylhexyloxy)-2-hydroxyl]phenyl}-6-(4-methoxyphenyl)-1,3,5-triazine (CAS No. 103 597-45-, 187 393-00-6).

Further suitable UV filters are also methoxyflavones corresponding to the earlier German patent application DE-A-10232595.

Organic UV filters are generally incorporated into cosmetic formulations in an amount of from 0.5 to 20 percent by weight, preferably 1-15%.

Conceivable inorganic UV filters are those from the group consisting of the titanium dioxides, such as, for example, coated titanium dioxide (for example Eusolex® 1-2000, Eusolex® 1-AQUA, Eusolex® 1-AVO), zinc oxides (for example Sachtotec®), iron oxides and also cerium oxides. These inorganic UV filters are generally incorporated into cosmetic compositions in an amount of from 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-iso-propyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

The compositions according to the invention containing UV-filter compounds are preferably sun protecting compositions. Such compositions may preferably contain pearlescent pigments according to claim 1 coated with a further protection layer consisting of $SiO_2$ as described in EP 1 725 301 A1, which is incorporated by reference therein.

The compositions according to the invention may in addition comprise further conventional skin-protecting or skin-care active ingredients. These may in principle be any active ingredients known to the person skilled in the art.

Particularly preferred active ingredients are, for example, also so-called solutes. These are substances which are involved in the osmoregulation of plants or microorganisms and can be isolated from these organisms. The generic term compatible solutes here also encompasses the osmolytes described in German Patent Application DE-A10133202. Suitable osmolytes are, for example, the polyols, methylamine compounds and amino acids and respective precursors thereof. Osmolytes in the sense of German Patent Application DE-A-101 33202 are, in particular, substances from the group consisting of the polyols, such as, for example, myo-inositol, mannitol or sorbitol, and or one or more of the osmolytically active substances mentioned below:

taurine, choline, betaine, phosphorylcholine, glycerophosphorylcholines, glutamine, glycine, α-alanine, glutamate, aspartate and proline. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps. Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate DGP), 3-mannosyl glycerate (firoin), 3-mannosyl glyceramide (firoin-A) and or dimannosyl diinositol phosphate (DMTP) or an optical isomer, derivative, for example an acid, a salt or ester of these compounds, or combinations thereof.

Of the pyrimidine carboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacteria cells. Pharmaceutical products, such as nonglycosylated, pharmaceutically active peptides and proteins, for example t-PA, can also be protected with ectoin or its derivatives.

In respect of the cosmetic applications, particular mention should be made of the use of ectoin and ectoin derivatives for the care of aged, dry or irritated skin.

Thus, European patent application EP-A-0 671 161 describes, in particular, that ectoin and hydroxyectoin are employed in cosmetic compositions, such as powders, soaps, surfactant-containing cleansing products, lipsticks, rouge, make-up, care creams and sunscreen preparations.

In a further, likewise preferred embodiment of the present invention, the composition according to the invention comprises at least one self-tanning agent.

Advantageous self-tanning agents which can be employed are, inter alia: glycerol aldehyde, hydroxymethylglyoxal, γ-dialdehyde, erythrulose, 6-aldo-D-fructose, ninhydrin, 5-s hydroxy-1,4-naphtoquinone, 2-hydroxy-1,4-naphtoquinone or 1,3-dihydroxyacetone (DHA).

The inventive effect pigments and further active ingredients can be incorporated into cosmetic or dermatological compositions in the customary manner. Suitable compositions are those for external use, for example in the form of a cream, lotion or gel or as a solution which can be sprayed onto the skin. Suitable for internal use are administration forms such as capsules, coated tablets, powders, tablet solutions or solutions.

Use forms of the compositions according to the invention that may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary carriers, assistants and, if desired, further active ingredients may be added to the composition.

Preferred assistants can be selected from the group consisting of preservatives, antioxidants, stabilisers, solubilisers, vitamins, colorants and odour improvers.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances. Surfactant-containing cleansing products may comprise the customary carriers, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, ailcylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic use forms are body powder, powder make-up, emulsion make-up, wax make-up, eye-shadow, foundation, lip gloss, lip liner, lip-stick, lip-care-stick, liquid eyeliner, mascara, mousse, rouge, hair shampoo, nail polish, eye liner, shower gel, body lotion, sunscreen, pre-sun preparations or after-sun preparation.

The preferred composition forms according to the invention also include, in particular, emulsions. Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and or unsaturated, branched and or unbranched alkanecarboxylic acids having a chain length of from 3 to 30 carbon atoms and saturated and or unsaturated, branched and or unbranched alcohols having a chain length of from 3 to 30 carbon atoms, or from the group consisting of esters of aromatic carboxylic acids and saturated and or unsaturated, branched and or unbranched alcohols having a chain length of from 3 to 30 carbon atoms.

Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethyl-hexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated and unsaturated, branched and unbranched alcohols, and fatty acid triglycerides, specifically the triglycerol esters of saturated and or unsaturated, branched and or unbranched alkanecarboxylic acids having a chain length of from 8 to 24, in particular 12 to 18, carbon atoms. The fatty acid triglycerides may advantageously be selected, for example from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$- alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil which can be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane). Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, mono-ethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants. The hydrophilic surfactants are preferably selected from the group consisting of the alkylglucosides, acyllactylates, betaines and coconut amphoacetates.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

A preferred example for a acyllactylates is sodium isostearyl lactylate, for example the product Pathionic® ISL from the American Ingredients Company.

A preferred example for a betaine is capramidopropylbetaine, for example the product lego® Betain 810 from Th. Goldschmidt AG.

A coconut amphoacetate which is advantageous for the purposes of the invention is, for example, sodium coconut amphoacetate, as available under the name Miranole Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions are applied in sufficient amount to the skin and or hair in the usual manner for cosmetics.

Cosmetic and dermatological compositions according to the invention may exist in various forms. Thus, they may be, for example, a solution, a water-free composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoin in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner. Emulsifiers that can be used are, for example, the known W/O and O/W emulsifiers. It is advantageous to use further conventional co-emulsifiers in the preferred O/w emulsions according to the invention.

Co-emulsifiers which are advantageous according to the invention are, for example, 0/w emulsifiers, principally from the group consisting of the substances having HLB values of 11-16, very particularly advantageously having HLB values of 14.5-15.5, so long as the O/w emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth20), polyethylene glycol (12) isostearyl ether (isostearethy12), polyethylene glycol (13) isostearyl ether (isostearethy13), polyethylene glycol (14) isostearyl ether (isosteareth14), polyethylene glycol (15) isostearyl ether (isosteareth15), polyethylene glycol (16) isostearyl ether (isosteareth16), polyethylene glycol (17) isostearyl ether (isosteareth17), polyethylene glycol (18) isostearyl ether (isosteareth18), polyethylene glycol (19) isostearyl ether (isosteareth19), polyethylene glycol (20) isostearyl ether (isosteareth20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth- 16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstcaryl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group: polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (113) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate capririate, polyethylene glycol (20) glyceryl oleate, polyethylene glycol (20) glyceryl isostearate, polyethylene glycol (18) glyceryl oleate cocoate.

It is likewise favourable to select the sorbitan esters from the group consisting of polyethylene glycol (20) sorbitan monolaurate, polyethylene glycol (20) sorbitan munostearate, polyethylene glycul (20) surbitan munuisustearate, polyethylene glycol (20) sorbitan monopalmitate, polyethylene glycol (20) sorbitan monooleate.

Optional W/O emulsifiers, but ones which may nevertheless be advantageous for the purposes of the invention can be the following:
fatty alcohols having from 8 to 30 carbon atoms, monoglycerol esters of saturated and or unsaturated, branched and or unbranched alkanecarboxylic acids having a chain length of from 8 to 24 carbon atoms, in particular 12-18 carbon atoms, diglycerol esters of saturated and or unsaturated, branched and or unbranched alkanecarboxylic acids having a chain length of from 8 to 24 carbon atoms, in particular 12-18 carbon atoms, monoglycerol ethers of saturated and or unsaturated, branched and or unbranched alcohols having a chain length of from 8 to 24 carbon atoms, in particular 12-18 carbon atoms, diglycerol ethers of saturated and or unsaturated, branched and or unbranched alcohols having a chain length of from 8 to 24 carbon atoms, in particular 12-18 carbon atoms, propylene glycol esters of saturated and or unsaturated, branched and or unbranched ailcanecarboxylic acids having a chain length of from 8 to 24 carbon atoms, in particular 12-18 carbon atoms, and sorbitan esters of saturated and or unsaturated, branched and or unbranched alkanecarboxylic acids having a chain length of from 8 to 24 carbon atoms, in particular 12-18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

Preferred compositions according to the invention are particularly suitable for protecting human skin against ageing processes and against oxidative stress, i.e. against damage by free radicals, as are produced, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surfactants, emulsifiers, preservatives, antifoams, perfumes, waxes, lanolin, propellants, dyes and or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. The composition may comprise various adjuvants used in this type of composition, such as surfactants, thickeners, polymers, softeners, preservatives, foam stabilisers, electrolytes, organic solvents, silicone derivatives, oils, waxes, antigrease agents, dyes and or pigments which colour the composition itself or the hair, or other ingredients usually used for hair care.

The compositions according to the invention can be prepared here with the aid of techniques which are well known to the person skilled in the art.

If the inventive cosmetic composition including the new pearlescent pigments used in accordance with the invention are films, a preferred use is the use thereof as or in artificial nails. The present application therefore furthermore relates to an artificial nail comprising the pearlescent pigments based on a new glass flake composition.

Thus, for example, a film comprising the effect pigments based on a new glass flake composition can, after cutting to match the size of the individual fingernail or toenail, be detached from the support sheet and applied to the fingernail toenail and subsequently fixed using clear nail varnish. Alternatively, the films may themselves be provided with an adhesive layer, so that subsequent varnishing is unnecessary. Placing of the film in a varnish before application to the fingernail is also a variant of the present invention in which subsequent varnishing is unnecessary.

Furthermore, the effect pigments based on a new glass flake composition can also be employed in a cosmetic composition like varnishes, such as UV-curable acrylic varnishes, which are used for the production of artificial nails.

A further use of the effect pigments based on a new glass flake composition which is preferred in accordance with the invention is use in nail-care compositions, in particular nail varnishes.

Nail-care compositions, in particular in the form of nail varnishes, are amongst the most-used decorative cosmetic compositions. They usually comprise a synthetic resin as film former and inorganic or organic pigments or dyes. The nail varnishes are intended to exhibit high gloss, high hardness and good adhesion to keratin-containing substances, such as fingernails, and to dry rapidly at room temperature to give a non-tacky, uniform film. The high gloss and the good adhesion should be retained over the longest possible period. In order that the nail varnishes can be removed again using conventional nail varnish removers, the film-forming resins used must be soluble in water acetone mixtures. By contrast, the film-forming resins should be insoluble in water or water alcohol mixtures in order that the nail varnish is not dissolved on contact with water or during handling of conventional household chemicals.

Typical nail varnishes which are suitable for use in accordance with the invention essentially consist of solutions, suspensions or emulsions of certain substances. Particular mention should be made here of binders, such as nitrocellulose, or various synthetic resins, such as, in particular, polyacrylates, polymethacrylates, toluenesulfonamide-formaldehyde resins, toluenesulfonamide-epoxy resins, alkyd resins or polyvinyl acetate. Furthermore, nail varnishes usually comprise suitable solvents for the binders, with solvent mixtures usually being employed. Typical solvents, besides water, are alcohols, esters and ketones, such as, in particular, methyl, ethyl, propyl and butyl acetate, isopropyl alcohol and n-butyl alcohol. The nail varnishes may optionally be provided with further additives for forming the optical appearance, for example soluble dyes. In addition, the mixture may comprise plasticisers (such as, for example, camphor or dibutyl phthalate) and extenders (for example toluene or xylene). These nail varnishes cure through evaporation of the solvent and the other volatile constituents as a function of the layer thickness of the varnish, the temperature and the type of solvent. In addition, the curing time is also dependent on other influences (for example air flow).

Particular preference is given in accordance with the invention to water-based nail-care compositions which preferably comprise polyurethanes or polyacrylates as binder.

Besides water, water-based nail varnishes comprise water-soluble resins, such as, for example, polyurethane resins, acrylic resins, alkyd resins, epoxy resins or melamine resins. The resin here is preferably selected in such a way that it is water-soluble, appears white or transparent in water, is inexpensive and simple to process, is as far as possible non-combustible and is not toxic or hyperallergenic. It may furthermore be essential that the varnish dries rapidly and has good film-forming properties at temperatures from 10° C.

The cosmetic formulations of the present inventions can further comprise antistatic substances, fillers, binders, chelating agents, wetting agents, bleaching agents, cosmetic oils, tensides, odor agents, flavour additives, reduction agents, opacifiers or viscosity regulation agents.

The cosmetic formulations of the present invention consist preferably a body powder, face powder, pressed powder, loose powder, face make-up such as tinted day cream, powder cream, cream make up, powder make-up, emulsion make-up, wax make-up, foundation, mousse, rouge or blush, eye make-up such as eye shadow, mascara, eyeliner, liquid eyeliner, eyebrow pencil, lip care preparation, lipstick, lip gloss, lip liner, hair care preparation such as hair shampoo, rinse-off or leave-on hair conditioner, perm, hair setting preparation, hair fixatives such as hair spray, hair mousse, hair gel, hair wax, permanent or semi-permanent hair dye, temporary hair dye, skin care preparation such as body lotion, body cream, face lotion, face cream, gel, sun care preparation such as sunscreen, pre-sun preparations or after-sun preparation, insect repellent, self tanning preparation, nail polish, skin cleansing preparation such as shower gel, face cleansing preparation or face peeling.

Even without further comments, it is assumed that a person skilled in the art will be able to utilise the above description in its broadest scope. The preferred embodiments should therefore merely be regarded as descriptive disclosure which is absolutely not limiting in any way. The complete disclosure content of all applications and publications mentioned above and below is incorporated into this application by way of reference. The following examples are intended to illustrate the present invention. However, they should in no way be regarded as limiting. All compounds or components which can be used in the compositions are either known and commercially available or can be synthesised by known methods.

EXAMPLES

I Preparations of Pearlescent Pigments

Example 1

200 g of glass flakes (supplied by Glassflakes Ltd. Forster Street Leeds LS10 1PW, United Kingdom) having a composition as specified in Table A with a mean particle thickness of 1 μm and particle diameters in the range of 50-150 μm and a $d_{50}$ of 88 μm were dispersed in 2 l of de-ionized water and the suspension was heated up 80° C. under turbulent stirring. Subsequently, the pH was adjusted to 1.9 using diluted hydrochloric acid and an acidic solution of 3 g $SnCl_4 \ast 5H_2O$ in 60 ml of diluted hydrochloric acid was added to the suspension within 60 minutes. Simultaneously, a solution of sodium hydroxide (10% W/W in water) was metered in order to keep a constant pH of 1.9. After the addition of the tin compound, the reaction mixture was stirred for 15 min to complete the precipitation. Then, the pH is lowered to 1.6 using diluted hydrochloric acid and a solution of $TiCl_4$ in water (400 g $TiCl_4$/l) was added to the suspension with 0.33 ml/min. The pH value was kept constant at 1.6 by co-dosage of sodium hydroxid (10% WAN in water). After 4 h a brilliant silver tone was achieved. The addition of the $TiCl_4$ solution was stopped and the reaction mixture was stirred for additional 15 minutes. After separation of the solids by filtration, the filter cake was washed using de-ionized water and calcined for 30 minutes at 650° C.

A highly brilliant pearlescent pigment with silver-white reflection colour is obtained. According to X-ray powder diffractometric analysis, the crystal modification of the $TiO_2$ is pure rutile.

TABLE A

| * Composition (X-ray analysis): | |
| --- | --- |
| $SiO_2$: | 68.6 wt.-% |
| $Al_2O_3$: | 4.1 wt.-% |
| CaO: | 1.8 wt.-% |
| MgO: | 1.2 wt.-% |
| $K_2O$: | 2.0 wt.-% |
| $Na_2O$: | 10 wt.-% |
| $B_2O_3$: | 9.9 wt.-% |
| $TiO_2$: | 1.6 wt.-% |
| $ZrO_2$: | 0.1 wt.-% |

Comparative Example 2

The same procedure as in example 1 was repeated using glass flakes of an ECR-Glass composition having a composition as specified in Table B with the same particle sizes of 50-150 μm and a $d_{50}$ of 87 μm.

TABLE B

| Composition according to manufacturer (Glassflakes Ltd. Forster Street Leeds LS10 1PW, United Kingdom): | |
| --- | --- |
| $SiO_2$: | 64-70 wt.-% |
| $Al_2O_3$: | 3-6 wt.-% |
| CaO: | 3-7 wt.-% |

TABLE B-continued

| Composition according to manufacturer (Glassflakes Ltd. Forster Street Leeds LS10 1PW, United Kingdom): | |
| --- | --- |
| MgO: | 1-4 wt.-% |
| $K_2O$: | 0-3 wt.-% |
| $Na_2O$: | 12-13 wt.-% |
| $B_2O_3$: | 2-5 wt.-% |
| $TiO_2$: | 0-3 wt.-% |
| $ZrO_2$: | — |
| ZnO: | 1-5 wt.-% |

Example 3

Analogous to example 1, but the $TiCl_4$-solution was added for 23 h with 0.33 ml/min leading to a pearlescent pigment with intensive red interference color.

Comparative Example 4

Commercially available pearlescent pigment Reflecks Sparkling Red (BASF-Catalysts).

Comparative Example 5

Commercially available pearlescent pigment Miraval 5422 Magic Red (MERCK).

The pigments of examples 1 and 3 and of comparative examples 2, 4 and 5 were mixed into conventional nitrocellulose laquer (Erco Bronzelack, Dr. Renger, Germany) and draw-downs on contrast paper were made. The gloss was measured at 60° using a Micro-Tri-Gloss (Byk-Gardner) instrument. The results are shown in table 1.

TABLE 1

| Sample | Gloss (60°), black background | Gloss (60°), white background |
| --- | --- | --- |
| Example 1 | 102.5 (±1.2) | 105.5 (±0.2) |
| Comparative example 2 | 95.5 (±0.2) | 100.5 (±0.6) |
| Example 3 | 79.9 | — |
| Comparative example 4 | 65.0 | — |
| Comparative example 5 | 58.4 | — |

The gloss of the pearlescent pigment of example 1 is significantly higher than the comparative example 2. Both samples exhibit a silver interference color and similar particle size, particle size distribution and thicknesses.

Within the red interference color pigments of example 3 and comparative examples 4 and 5 the inventive pigment exhibits also a higher gloss than the pigments of the state of the art. The differences in the gloss are even more pronounced compared to the silver pigments.

Example 6

The early stages of precipitation of $SnO_2$ and of $TiO_2$ were analysed. For this purpose, example 1 was essentially repeated, however small samples of coated glass flakes were taken at defined reaction times of the reaction mixture (Table 1). The coating with $TiO_2$ was finally stopped already at 2 hours.

The samples were dried under vacuum at 60° C. The last sample was calcined for 30 minutes at 650° C.

The surface of the samples were analysed by SEM at different magnifications.

Comparative Example 7

Comparative Example 7 was essentially repeated using the glass flakes of an ECR-Glass of comparative example 2 as substrate and samples were taken out at the same reaction times like in example 6. These samples were dried and then analyzed by SEM.

TABLE 2

Reaction stages and times of samples taken of

| Sample number | Reaction stage and time Example 6 | Reaction stage and time Comparative example 7 |
|---|---|---|
| a | $SnO_2$ coating/ 15 min | $SnO_2$ coating/ 15 min |
| b | $TiO_2$ coating 5 min | $TiO_2$ coating 5 min |
| c | $TiO_2$ coating 5 min | $TiO_2$ coating 5 min |
| d | $TiO_2$ coating 15 min | $TiO_2$ coating 15 min |
| e | $TiO_2$ coating 30 min | $TiO_2$ coating 30 min |
| f | $TiO_2$ coating 60 min | $TiO_2$ coating 60 min |
| g | $TiO_2$ coating 120 min | $TiO_2$ coating 120 min |

In FIG. 1a,b the SEM pictures of selected samples of example 6 and comparative example 7, compiled in Table 2, are compared. It can be clearly seen that at the very early stages of coating the glass flakes with metal oxides, e.g. 15 min after $SnO_2$ coating and 5 min after $TiO_2$ coating (FIG. 1a), the oxide grains of example 6 are much smaller compared with comparative example 7. In FIG. 1b one can depict that the oxide grains grow larger in the course of further coating. However, the oxide grains for example 6 remain always significantly smaller compared to the ones of comparative example 7. Even after calcining (sample g) the difference remains. Consequently, even recrystallisation processes of the $TiO_2$ layers which might occur at calcining do not affect the differences in the dimensions of the oxide grains which existed already before. In sample g a lot of oxide grains with sizes in the 100 nm range and larger can be observed for comparative example 6. Such particles do already significantly reduce the gloss of this pigment. Sample g of example 6, however, doesn't show such large oxide particles.

It is noted, that sample g corresponds to samples which were coated with titania for 2 hours. A silver tone is achieved at 4 hours coating time, however. Thus sample g represents a "pre-silver" pearlescent pigment. Silver is known to be the first colour tone of the interference series followed by gold, red, blue, green and than the second order colours. Consequently, these coloured pearl pigments will exhibit even larger oxide grains and gloss-reducing scattering effects will also increase. Thus the benefits of the smaller oxide grains of the inventive pearlescent pigments will accordingly increase at larger metal oxide thickness.

II Tests Regarding Skin Feeling

IIa Triangular Test

Comparative Example 8

Commercially available Firemist Blue (Pearlescent pigment from BASF Catalysts) for cosmetic use.

The pigments of example 1 and of comparative example 8 were compared in a triangular test. This test is designated to show whether two pigments exhibit a difference in skin feeling.

Procedure:

Three coded samples of the two different pigments where applied on the forearm of the panellist. The panellists arms where placed in a box to prevent the panellist from looking at the arms. Two of the samples are the same, one sample is different. The panellist was asked to touch the samples and to answer the following question:

Which two samples are similar?

Result:

11 out of 20 panellist answered correctly.

This shows that the samples of example 1 and of comparative example 8 are significantly different (based on a significance level of $\alpha=0.05$)

IIb Panel Tests Skin Feeling

Panel tests regarding the skin feeling have conducted with the pigments of example 1 and comparative example 2.

Procedure:

Two coded samples where applied on the forearm of the panellist. The panellists arms where placed in a box to prevent the panellist from looking at the arms. The panellist was asked to touch the samples and to compare the two samples in regards to the parameter "smoothness" and ranked them from 0 (smooth)-10 (rough). 20 panellists have been evaluated.

This procedure is standard in cosmetic industry and described in: Morten C. Meilgaard/Gail Vance Civille/B. Thomas Carr "Sensory Evaluation Techniques"; CRC Press, $4^{th}$ edition, Chapter 7: Attribute Difference Tests.

Result:

The statistical comparison of the mean values of the sample ranking shows that the two samples have a significantly different skin feel in terms of smoothness (based on a significance level of $\alpha=0.05$).

The pigments of example 1 have a significantly better skin feel than the pigments of comparative example 2.

III. Applications

With both pearlescent pigments, i.e. according to example 1 and comparative example 2, a number of cosmetic applications were prepared and compared (see 11. Applications).

Example 9

Body Powder

| INCI Name | Product Name | % W/W | Supplier |
|---|---|---|---|
| A | | 100.00 | |
| Mica | Silk Mica | 40.70 | www.vwr.com |
| Talc | Talc Powder | 18.00 | www.riedeldehaen.com |
| Boron Nitride | Softouch CCS 102 | 5.00 | www.advceramics.com |
| Nylon 12 | Orgasol 2002 D/Nat | 8.00 | www.atofinachemicals.com |
| Magnesium Stearate | Magnesium Stearate | 6.00 | www.sigmaaldrich.com |
| Methylparaben, Propylparaben | Rokonsal SSH-1 | 0.30 | www.biochema.com |
| Mica (and) Iron Oxides | Prestige ® Soft Bronze | 9.00 | www.eckart.net |

| INCI Name | Product Name | % W/W | Supplier |
|---|---|---|---|
| Pearlescent pigment according to example 1 | — | 2.00 | |
| Mica (and) Titanium Dioxide B | Prestige ® Magic Orange | 9.00 | www.eckart.net |
| Tridecyl Stearate (and) Tridecyl Trimellitate (and) Dipentaerythrityl Hexacaprylate/Hexacaprate | Lipovol MOS-130 | 2.00 | www.lipochemicals.com |

Procedure:
1. Mix the ingredients of phase A
2. Add phase B to Phase A
3. Mix well and fill into a vessel Comparative Example 10

Same Composition as Above Using Pearlescent Pigments of Comparative Example 2

The body powder of example 9 showed a better gloss and a softer skin feel compared to the composition with ECR-Glass flakes.

Example 11

Cream Eye Shadow

| INCI Name | Product Name | % W/W | Supplier |
|---|---|---|---|
| A | | 100.00 | |
| Castor Oil | Castor Oil | 31.70 | www.riedeldehaen.com |
| Octyl Palmitate | Liponate EHP | 6.00 | www.lipochemicals.com |
| Cocos Nucifera (Coconut) Oil | Lipovol C-76 | 7.00 | www.lipochemicals.com |
| Bees Wax | Ewacera 12 | 6.00 | www.wagnerlanolin.com |
| Isopropyl Lanolate | Ewalan IP | 5.00 | www.wagnerlanolin.com |
| Persea Gratissima (Avocado) Oil and Hydrogenated Avocado Oil | Avocado Butter | 7.00 | www.impag.de |
| Magnesium Stearate | Magnesium Stearate | 3.00 | www.sigmaaldrich.com |
| Bis-Hydroxyethoxypropyl Dimethicone | Dow Corning 5562 Carbinol Fluid | 7.00 | www.dowcorning.com |
| Dimethicone/Vinyl Dimethicone Crosspolymer and Silica | Dow Corning 9701 Cosmetic Powder | 5.00 | www.dowcorning.com |
| Phenoxyethanol (and) Methylparaben (and) Ethylparaben (and) Butylparaben | Uniphen P-23 | 0.30 | www.induchem.com |
| B | | | |
| Mica (and) Iron Oxides | Prestige ® Soft Bronze | 21.00 | www.eckart.net |
| Pearlescent pigment according to example 1 | | 1.00 | |

Procedure:
1. Mix phase A and heat up to 85° C.
2. Pre-mix phase B
3. Add phase B to phase A while stirring
4. Pour into an appropriate container
5. Cool down to RT

Comparative Example 12

Same Composition as Above Using Pearlescent Pigments of Comparative Example 2

The cream eye shadow of example 11 showed a better gloss and a softer skin feel compared to the composition with ECR-Glass flakes.

Example 13

Foundation

| INCI Name | Product Name | % W/W | Supplier |
| --- | --- | --- | --- |
| A | | 100.00 | |
| Hydrogenated Polydecene | Ritadecene 20 | 9.00 | www.ritacorp.com |
| Caprylic/Capric Triglyceride | Liponate GC-K | 5.00 | www.lipochemicals.com |
| *Prunus Amygdalus Dulcis* (Sweet Almond) Oil | Sweet Almond Oil | 4.00 | www.jandekker.com |
| Caprylyl Trimethicone | SilCare Silicone 31M50 | 4.00 | www.clariant.com |
| Caprylyl Methicone | SilCare Silicone 41M15 | 3.00 | www.clariant.com |
| Steareth-2 | Volpo S2 | 1.60 | www.croda.com |
| Steareth-20 | Sympatens AS/200 G | 2.40 | www.kolb.ch |
| B | | | |
| Talc | Talc Powder | 4.50 | www.vwr.com |
| Mica (and) Iron Oxides | Prestige ® Soft Beige | 4.00 | www.eckart.net |
| Mica (and) Titanium Dioxide | Prestige ® Soft Silver | 1.00 | www.eckart.net |
| Pearlescent pigment according to example 1 | | 0.50 | |
| C | | | |
| Glycerin | Pricerine 9090 | 5.00 | www.brenntag.com |
| Water | Aqua | 55.20 | |
| Ammonium Acryloyldimehtyltaurate/VP Copolymer | Aristoflex AVC | 0.40 | www.simon-und-werner.com |
| D | | | |
| Propylene Glycol (and) Diazolidinyl Urea (and) Methylparaben (and) Propylparaben | Nipaguard PDU | 0.40 | www.simon-und-werner.com |

Procedure:

1. Heat phase A to 70° C. while stirring

2. Add the ingredients of phase B to phase A

3. Mix phase C well until Aristoflex is dissolved

4. Heat the mixture to 70° C.

5. Add phase C to phase AB

6. Cool down to 40° C. and add phase D

Comparative Example 14

Same Composition as Above Using Pearlescent Pigments of Comparative Example 2

The foundation of example 13 showed a better gloss and a softer skin feel compared to the composition with ECR-Glass flakes.

Example 15

Lip Gloss

| INCI Name | Product Name | % W/W | Supplier |
|---|---|---|---|
| A | | 100.00 | |
| Hydrogenated Polyisobutene (and) Ethylene/Propylene/Styrene Copolymer (and) Butylene/Ethylene/Styrene Copolymer | Versagel ME 750 | 79.00 | www.penreco.com |
| Simmondsia Chinensis (Jojoba) Seed Oil | Jojoba Oil - Natural/Golden | 2.00 | www.biochemica.com |
| Caprylyl Trimethicone | Silcare Silicone 31M50 | 7.00 | www.clariant.com |
| Stearyl Dimethicone | Silcare Silicone 41M65 | 3.20 | www.clariant.com |
| Hydrogenated Polydecene | Nexbase 2002 | 4.00 | www.jandekker.com |
| Isopropyl Myristate | Isopropyl Myristate | 4.50 | www.vwr.com |
| B | | | |
| Pearlescent pigment according to example 1 | | 0.10 | |
| Propylparaben | Propyl-4-hydroxybenzoat | 0.20 | www.sigmaaldrich.com |

Procedure
1. Heat phase A to 85° C.
2. Add phase B to phase A and mix until uniform
3. Pour into a lip gloss vessel

Comparative Example 16

Same Composition as Above Using Pearlescent Pigments of Comparative Example 2

The lip gloss of example 15 showed a better gloss compared to the composition with ECR-Glass flakes.

Example 17

Lip Liner

| INCI Name | Product Name | % W/W | Supplier |
|---|---|---|---|
| A | | 100.00 | |
| Hydrogenated Coco-Glycerides | Softisan 100 | 12.35 | www.sasolwax.com |
| Candelilla Wax | Ewacera 42 | 14.00 | www.wagnerlanolin.de |
| Magnesium Stearate | Magnesium Stearate | 6.00 | www.sigmaaldrich.com |
| Stearic Acid | Kortacid 1895 | 8.50 | www.akzonobel.com |
| Hydrogenated Coconut Oil | Lipex 401 | 8.00 | www.karlshamns.com |
| Cetyl Palmitate | Walrath synthetic | 7.00 | www.kahlwax.de |
| Caprylic/Capric Triglyceride | Liponate GC-K | 3.60 | www.lipochemicals.com |
| Soybean Glycerides (and) Butyrospermum Parkii | Lipex L'sens | 15.00 | www.karlshamns.com |
| Tocopheryl Acetate | D,L-Alpha-Tocopherolacetat | 0.25 | www.dsm.com |
| Methylparaben; Propylparaben | Rokonsal SSH-1 | 0.30 | www.biochema.com |
| B | | | |
| Mica (and) Titanium Dioxide (and) Ferric Ferrocyanide | Prestige ® Sapphire | 7.50 | www.eckart.net |
| Mica (and) Iron Oxides | Prestige ® Copper | 7.50 | www.eckart.net |
| Mica (and) Titanium Dioxide | Prestige ® Soft Silver | 5.00 | www.eckart.net |

| INCI Name | Product Name | % W/W | Supplier |
|---|---|---|---|
| Pearlescent pigment according to example 1 | | 5.00 | |

Procedure:
1. Heat phase A to 85° C.
2. Add phase B to phase A and mix until uniform
3. Poor into a Stick mold and cool

Comparative Example 18

Same Composition as Above Using Pearlescent Pigments of Comparative Example 2

The lip liner of example 17 showed a better gloss compared to the composition with ECR-Glass flakes.

Example 19

Lip-Stick

| INCI Name | Product Name | % W/W | Supplier |
|---|---|---|---|
| A | | 100.00 | |
| Carnauba Wax | Ewacera 34 | 4.50 | www.wagnerlanolin.de |
| Bees Wax | Ewacera 12 | 3.50 | www.wagnerlanolin.de |
| Candelilla Wax | Ewacera 42 | 4.00 | www.wagnerlanolin.de |
| Microcrystalline Wax | Parcera MW | 7.20 | www.paramelt.com |
| Cetyl Palmitate | Walrath synthetic | 2.00 | www.kahlwax.de |
| Hydrogenated Coco-Glycerides | Softisan 100 | 5.00 | www.sasolwax.com |
| Petrolatum | Penreco Blond | 5.80 | www.penreco.com |
| Cetearyl Octanoate | Luvitol EHO | 10.70 | www.basf.com |
| Tocopheryl Acetate | D,L-Alpha-Tocopherolacetat | 0.50 | www.dsm.com |
| Castor Oil | Castor Oil | 39.60 | www.riedeldehaen.com |
| B | | | |
| Mica (and) Iron Oxide | Prestige ® Fire-red | 16.00 | www.eckart.net |
| Pearlescent pigment according to example 1 | | 1.00 | |
| Methylparaben, Propylparaben | Rokonsal SSH-1 | 0.20 | www.biochema.com |

Procedure:
1. Heat phase A to 85° C.
2. Add phase B to phase A and mix until uniform
3. Poor into a lipstick mold at 75° C.

Comparative Example 20

Same Composition as Above Using Pearlescent Pigments of Comparative Example 2

The lip-stick of example 19 showed a better gloss and a better skin feeling compared to the composition with ECR-Glass flakes.

Example 21

Liquid Eyeliner

| INCI Name | Product Name | % W/W | Supplier |
|---|---|---|---|
| A | | 100.00 | |
| Water | Aqua | 68.70 | |
| Water/carbon black dispersion | MBD 201 | 3.00 | www.geotech.nl |
| Acrylates Copolymer | Covacryl E14 | 10.00 | www.lcw.fr |
| Magnesium Aluminium Silicate | Veegum HV | 1.00 | www.cherbsloeh.de |

-continued

| INCI Name | Product Name | % W/W | Supplier |
|---|---|---|---|
| B | | | |
| Propylene Glycol | 1,2 Propandiol | 3.00 | www.vwr.com |
| Triethanolamine | Triethanolamine | 1.40 | www.vwr.com |
| C | | | |
| Xanthan Gum | Keltrol T | 0.30 | www.cpkelco.com |
| D | | | |
| Pearlescent pigment according to example 1 | | 1.00 | |
| Mica | Silk Mica | 2.00 | www.vwr.com |
| E | | | |
| Stearic Acid | Kortacid 1895 | 2.80 | www.akzonobel.de |
| Glyceryl Stearate | Aldo MS K FG | 0.80 | www.lonza.com |
| Oleyl Alcohol | HD-Ocenol 90/95 V | 0.50 | www.biesterfeld.com |
| Phenoxyethanol (and) Methylparaben (and) Ethylparaben (and) Butylparaben | Uniphen P-23 | 0.50 | www.induchem.com |
| F | | | |
| Dimethicone (and) Trisiloxane | Dow Corning 2-1184 Fluid | 5.00 | www.dowchemicals.com |

Procedure:
1. Disperse Veegum in phase A
2. Stirr for 15 minutes
3. Add phase B to phase A
4. Add phase C to phase AB
5. Stirr for 10 minutes
6. Add phase D to phase ABC and heat to 75° C.
7. Heat phase E to 75° C.
8. Add phase E to phase ABCD
9. Cool down to 60° C. and add phase F Comparative Example 22

Same Composition as Above Using Pearlescent Pigments of Comparative Example 2

The eyeliner of example 21 showed a better gloss and a better skin feeling compared to the composition with ECR-Glass flakes.

Example 23

Mascara

| INCI Name | Product Name | % W/W | Supplier |
|---|---|---|---|
| A | | 100.00 | |
| Water | Aqua | 66.00 | |
| Propylene Glycol | 1,2 Propanediol | 1.50 | www.vwr.com |
| Pearlescent pigment according to example 1 | | 1.30 | |
| Cosmetic Black Oxide | C 33-134 Cosmetic Black Oxide | 7.00 | www.sunchemical.com |
| Caprylic/Capric Triglyceride | Liponate GC-K | 2.00 | www.lipochemicals.com |
| Hydroxyethylcellulose | Cellosize HEC QP-52000H | 0.30 | www.dow.com |
| Magnesium Alumium Silicate | Veegum HV | 1.80 | www.rtvanderbilt.com |
| B | | | |
| Carnauba Wax | Ewacera 34 | 3.00 | www.wagnerlanolin.de |
| Bees Wax | Ewacera 12 | 3.00 | www.wagnerlanolin.de |
| Glyceryl Stearate | Imwitor 960 K | 3.00 | www.sasolwax.xom |
| Cetyl Alcohol | Cetyl Alcohol | 3.80 | www.vwr.com |
| Polysorbate 60 | Tween 60 V | 1.00 | www.uniqema.com |
| PVP/VA Copolymer | Luviskol VA 64 | 2.00 | www.basf.com |

-continued

| INCI Name | Product Name | % W/W | Supplier |
|---|---|---|---|
| C | | | |
| Water | Aqua | 4.00 | |
| BHT | Tenox BHT Kosher | 0.10 | www.eastman.com |
| Methylparaben | Methyl-4-hydroxybenzoate | 0.20 | www.sigmaaldrich.com |

Procedure:
1. Heat phase A to 85° C. with stirring
2. Heat phase B to 85° C.
3. Mix phase B into phase A
4. Cool down to 55° C. while stirring
5. Add phase C and mix well
6. Fill into Mascara Set Comparative Example 24

Same Composition as Above Using Pearlescent Pigments of Comparative Example 2

The mascara of example 23 showed a better gloss and a better skin feeling compared to the composition with ECR-Glass flakes.

Example 25

Mousse

| INCI Name | Product Name | % W/W | Designated use |
|---|---|---|---|
| A | | 100.00 | |
| Cyclopentasiloxane | Dow Corning 245 Fluid | 8.60 | www.dowcorning.com |
| Hydrogenated Polyisobutene | MC 30 | 4.00 | www.sophim.com |
| Dimethicone (and) Dimethicone Crosspolymer | Dow Corning 9041 Silicone Elastomer Blend | 34.14 | www.dowcorning.com |
| Squalane | Squalane | 5.74 | www.impag.de |
| Isononyl Isononanoate | Dermol 99 | 10.16 | www.alzointernational.com |
| Hydrogenated Jojoba Oil | Jojoba Butter LM | 2.15 | www.desertwhale.com |
| Hydrogenated Jojaba Oil | Jojoba Butter HM | 1.00 | www.desertwhale.com |
| C30-45 Alkyl Methicone (and) C30-45 Olefin | Dow Corning AMS-C30 Cosmetic Wax | 1.15 | www.dowcorning.com |
| Stearyl Dimethicone | Dow Corning 2503 Cosmetic Wax | 0.47 | www.dowcorning.com |
| Cyclopentasiloxane (and) Polypropylsilsesquioxane | Dow Corning 670 Fluid | 5.00 | www.dowcorning.com |
| B | | | |
| Dimethicone/Vinyl Dimethicone Crosspolymer | Dow Corning 9506 Powder | 16.02 | www.dowcorning.com |
| Silica Dimethyl Silylate | Covasilic 15 | 0.17 | www.lcw.fr |
| Talc | Talc Powder | 5.00 | www.riedeldehaen.com |
| Mica (and) Titanium Dioxide (and) Iron Oxides | Prestige ® Soft Beige | 5.00 | www.eckart.net |
| Pearlescent pigment according to example 1 | | 1.00 | |
| C | | | |
| Propylene Glycol, Diazolidinyl Urea, Methylparaben, Propylparaben | Germaben II | 0.40 | www.ispcorp.com |

Procedure:
1. Mix ingredients of phase A and heat until melted
2. Pre-mix phase B with speed mixer (2400 rpm, 1 min)
3. Add half part of molten phase A to phase B and mix with speed mixer (2400 rpm, 30 s)
4. Add reminder of phase A to phase B and mix with speed mixer (2400 rpm, 30 s)
5. Add phase C and mix with speed mixer (2400 rpm, 30 s)
6. Cool down to room temperature

Comparative Example 26

Same Composition as Above Using Pearlescent Pigments of Comparative Example 2

The mousse of example 25 showed a better gloss and a better skin feeling compared to the composition with ECR-Glass flakes.

Example 27

Nail Polish

| INCI Name | Product Name | % W/W | Supplier |
|---|---|---|---|
| A | | | |
| Pearlescent pigment according to example 1 | | 2.00 | www.eckart.net |
| B | | | |
| International Lacquers Nailpolish & Care Base 359 | Butylacetat (and) Ethylacetat (and) Nitrocellulose (and) Isopropyl Alcohol | 98.00 | www.internationallacquers.lu |

Procedure:
1. Mix phase A with B with stirring
2. Pour into an appropriate container

Comparative Example 28

Same Composition as Above Using Pearlescent Pigments of Comparative Example 2

The nail polish of example 27 showed a better gloss compared to the composition with ECR-Glass flakes.

Example 29

Pressed Eye Shadow

| INCI Name | Product Name | % W/W | Supplier |
|---|---|---|---|
| A | | 100.00 | |
| Mica | Silk Mica | 17.00 | www.vwr.com |
| Boron Nitride | Softouch CCS 102 | 2.50 | www.advceramicscos.com |
| Talc | Talc Powder | 23.50 | www.riedeldehaen.com |
| Zinc Stearate | Kemilub EZ-V | 7.00 | www.undesa.com |
| Mica (and) Iron Oxides | Prestige ® Bright Fire-red | 39.00 | www.eckart.net |
| Pearlescent pigment according to example 1 | | 1.00 | |
| B | | | |
| Dimethicone | Dow Corning ® 200 Fluid 5 cst | 5.00 | www.dowcorning.com |
| Cyclomethicone (and) Dimethicone Crosspolymer | Dow Corning ® 9040 Elastomer | 5.00 | www.dowcorning.com |

Procedure:
1. Mix phase A
2. Add phase B and stir until homogeneous
3. Press eye shadow at 150 bar for 30 min

Comparative Example 30

Same Composition as Above Using Pearlescent Pigments of Comparative Example 2

The eye shadow of example 29 showed a better gloss compared to the composition with ECR-Glass flakes.

Example 31

Pressed Powder

| INCI Name | Product Name | % W/W | Supplier |
|---|---|---|---|
| A | | 100.00 | |
| Talc | Talc Powder | 51.70 | www.riedeldehaen.com |
| Zinc Stearate | Kemilub EZ-V | 5.00 | www.undesa.com |
| Methylparaben, Propylparaben | Rokonsal SSH-1 | 0.30 | www.biochema.com |
| Polyethylene | Asensa CL 111 | 20.50 | www.honeywell.com |
| Silica | Syloblanc 34 | 1.50 | www.gracedavision.com |
| Mica (and) Titanium Dioxide | Prestige ® Soft Silver | 6.00 | www.eckart.net |
| Mica (and) Titanium Dioxide (and) Iron Oxides | Prestige ® Soft Beige | 11.00 | www.eckart.net |
| Pearlescent pigment according to example 1 | | 1.00 | |
| B | | | |
| Octyl Palmitate | Liponate EHP | 3.00 | www.lipochemicals.com |

Procedure:
1. Mix phase A
2. Add phase B and stir until homogeneous
3. Press eye shadow at 150 bar for 30 min

Comparative Example 32

Same Composition as Above Using Pearlescent Pigments of Comparative Example 2

The pressed powder of example 31 showed a better gloss compared to the composition with ECR-Glass flakes.

Example 33

Shower Gel

| INCI Name | Product Name | % W/W | Supplier |
|---|---|---|---|
| A | | 100.00 | |
| Pearlescent pigment according to example 1 | | 0.01 | |
| Water | Aqua | 67.94 | |
| Blue 1 (0.5% aqueous solution) | FD&C Blue No. 1 | 0.10 | www.sunchemicals.com |
| Acrylates/C10-30 Alkyl Acrylate Crosspolymer | Carbopol ETD 2020 | 1.00 | www.noveon.com |
| Propylene Glycol | 1,2-Propanediol | 1.00 | www.vwr.com |
| B | | | |
| TEA-Lauryl Sulfate | Texapon T 42 | 22.00 | www.cognis.com |
| Cocamide Dea | Rewomid DC 212 S | 3.00 | www.degussa.com |
| Cocamidopropyl Betaine | Tego Betain F 50 | 4.00 | www.cognis.com |
| Disodium EDTA | Edeta BD | 0.05 | www.basf.com |

-continued

| INCI Name | Product Name | % W/W | Supplier |
|---|---|---|---|
| C | | | |
| Triethanolamine | Triethanolamine | 0.30 | www.vwr.com |
| Phenoxyethanol, Ethylhexylglycerin | Euxyl PE 9010 | 0.60 | www.schuelke-mayr.com |

Procedure:
1. Disperse Carbopol in phase A
2. Heat phase to 65° C.
3. Add one by one the ingredients of phase B
4. Cool down and continue to stir. When 40-45° C. are reached add phase C Comparative Example 34

Same Composition as Above Using Pearlescent Pigments of Comparative Example 2

The shower gel of example 33 showed a better gloss compared to the composition with ECR-Glass flakes.

Example 35

Styling Soft Wax

| INCI Name | Product Name | % W/W | Supplier |
|---|---|---|---|
| A | | 100.00 | |
| Pearlescent pigment according to example 1 | | 0.10 | |
| Water | Aqua | 53.40 | |
| Propylene Glycol | 1,2 Propanediol | 2.00 | www.vwr.com |
| Glycerin | Pricerine 9090 | 7.00 | www.uniqema.com |
| Methoxy PEG/PPG-7/3 Aminopropyl Dimethicone | Abil Soft AF 100 | 0.50 | www.degussa.com |
| B | | | |
| Isosteareth-20 | Procol IS-20 | 14.50 | www.protameen.com |
| Laureth-4 | Genapol LA 040 | 10.00 | www.clariant.com |
| Paraffinum Liquidium | Paraffinum Liquidium | 6.00 | www.heess.de |
| C12-15 Alkyl Benzoate | Sympatens-LBZ | 6.00 | www.kolb.ch |
| C | | | |
| Phenoxyethanol (and) Methylparaben (and) Butylparaben (and) Ethylparaben (and) Propylparaben (and) Isobutylparaben | Phenonip | 0.40 | www.clariant.com |
| Fragrance | Cool Floral OA D | 0.10 | www.bell-europe.com |

Procedure:
1. Heat phase A and B seperatly to 90° C.
2. Add phase B to phase A while stirring
3. Cool down to 55° C.
4. Add phase C and fill into jar

Comparative Example 36

Same Composition as Above Using Pearlescent Pigments of Comparative Example 2

The Styling Soft Wax of example 35 showed a better gloss compared to the composition with ECR-Glass flakes.

Example 37

Sun Protection Cream

| INCI Name | Product Name | % W/W | Supplier |
|---|---|---|---|
| A | | 100.00 | |
| Sorbitan Stearate (and) Methyl Glucose Sesquistearte | Sympatens-O/2500 G | 5.00 | www.kolb.ch |
| Stearic Acid | Kortacid 1895 | 4.00 | www.akzonobel.com |
| Octyldodecanol | Eutanol G | 9.00 | www.cognis.com |
| Caprylic/Capric Triglyceride | Liponate GC-K | 10.00 | www.lipochemicals.com |
| Cetearyl Alcohol | Lanette O | 2.00 | www.cognis.com |
| *Macadamia ternifolia* Seed Oil | *Macadamia* Nut Oil | 3.20 | www.jandekker.com |
| Octyl Methoxycinnamate | Parsol MCX | 1.00 | www.dsm.com |
| Butyl Methoxydibenzoylmethane | Parsol 1789 | 5.00 | www.roche.com |
| B | | | |
| Pearlescent pigment according to example 1 | | 0.70 | |
| Water | Aqua | 56.35 | |
| Glycerin | Pricerine 9090 | 3.20 | www.uniqema.com |
| C | | | |
| Phenoxyethanol (and) Methylparaben (and) Ethylparaben (and) Butylparaben | Uniphen P-23 | 0.40 | www.induchem.com |
| Fragrance | Nivamar BM | 0.15 | www.bell-europe.com |

Procedure:
1. Heat phase A and B seperately to 80° C.
2. Add phase A to phase B while stirring
3. Cool down to 45° C.
4. Add phase C

Comparative Example 38

Same Composition as Above Using Pearlescent Pigments of Comparative Example 2

The sun protection cream of example 37 showed a better gloss compared to the composition with ECR-Glass flakes.

Example 39

Transparent Lipstick

| INCI Name | Product Name | % W/W | Supplier |
|---|---|---|---|
| A | | 100.00 | |
| Ethylenediamine/Hydrogenated Dimer Dilinoleate Copolymer Bis-Di-C14-18 Alkyl Amide | Sylvaclear A2614V | 28.00 | www.arizonachemical.com |
| Bis-Stearyl Ethylenediamine/ Neopentyl Glycol/Hydrogenated Dimer Dilinoleate | Sylvaclear C75V | 28.00 | www.arizonachemical.com |
| Paraffinum Liquidum | Paraffinum Liquidum | 13.80 | www.heess.de |
| *Macadamia Integrifolia* Seed Oil | Floramac Hawaiian *Macadamia* Oil-Refined | 10.00 | www.floratech.com |
| Isopropyl Myristate | Isopropyl Myristate | 6.00 | www.vwr.com |
| C12-15 Alkyl Benzoate | Sympatens-LBZ | 6.00 | www.kolb.ch |
| Caprylic/Capric Triglyceride | Miglyol 812 | 7.00 | www.sasolwax.com |
| Propylparaben | Propyl-4-hydroxybenzoat | 0.20 | www.sigmaaldrich.com |

-continued

| INCI Name | Product Name | % W/W | Supplier |
|---|---|---|---|
| B | | | |
| Pearlescent pigment according to example 1 | | 1.00 | t |

Procedure:
1. Heat phase A to 85° C.
2. Add phase B to phase A and mix
3. Poor into lipstick mould at 75° C.

Comparative Example 40

Same Composition as Above Using Pearlescent Pigments of Comparative Example 2

The Transparent lip-stick of example 39 showed a better gloss compared to the composition with ECR-Glass flakes.

Example 41

Body Lotion Water-In-Silicone

| INCI Name | Product Name | % W/W | Supplier |
|---|---|---|---|
| A | | 100.00 | |
| Cyclopentasiloxane (and) Dimethiconol | Dow Corning 1501 | 11.50 | www.dowcorning.com |
| Cyclopentasiloxane | Dow Corning 245 | 5.75 | www.dowcorning.com |
| Cyclopentasiloxane (and) PEG/PPG/— 18/18 Dimethicone | Dow Corning 5225 C | 13.80 | www.dowcorning.com |
| C 30-45 Alkyl Methicone | Dow Corning Cosmetic Wax AMS-C30 | 3.45 | www.dowcorning.com |
| Pearlescent pigment according to example 1 | | 0.70 | |
| C | | | |
| Polysorbate 20 | Tween 20 | 0.60 | www.uniqema.com |
| Phenoxyethanol (and) Methylparaben (and) Ethylparaben (and) Butylparaben | Uniphen P-23 | 0.35 | www.induchem.com |
| Sodium Chloride | Sodium Chloride | 0.75 | www.vwr.com |
| Water | Aqua | 63.10 | |

Procedure:
1. Mix phase A and heat up to 75° C.
2. Mix phase B and heat up to 70° C.
3. Add phase B slowly to phase A under homogenisation
4. Cool down while stirring Comparative Example 42

Same Composition as Above Using Pearlescent Pigments of Comparative Example 2

The Body Lotion of example 41 showed a better gloss compared to the composition with ECR-Glass flakes.

What is claimed is:

1. A cosmetic composition comprising an effect pigment based on a glass flake as a substrate with a coating, said coating comprising at least one layer of at least one high refractive material, said material having at least one of a refractive index of at least 1.8, and a semitransparent metal coating,
wherein said glass flakes comprise the following composition:
67-73 wt.-% of silicon oxide;
4-7 wt.-% of aluminum oxide;
0.5-2.5 wt.-% of calcium oxide;
6-11 wt.-% of sodium oxide;
8.5-14 wt.-% of boron oxide;
0.5-2.5 wt.-% of titanium oxide;
0.1-1.5 wt.-% of zirconium oxide; and
1-4 wt.-% of at least one of potassium oxide, lithium oxide, and magnesium oxide,
wherein the wt.-% is based on the weight of said glass flakes;
wherein the difference between the refractive index of the glass flakes and the subsequently applied at least one layer of high refractive material is at least 0.6;
wherein the at least one high refractive material is selected from the group consisting of metal chalcogenides, metal oxyhalides, metal nitrides, metal carbides, semitransparent metals and mixtures thereof; and
wherein components used in producing said glass flakes meet at least one of the following criteria:
(a) the silicon oxide is $SiO_2$;
(b) the aluminum oxide is $Al_2O_3$;
(c) the calcium oxide CaO;
(d) the sodium oxide is $Na_2O$;
(e) the boron oxide is $B_2O_3$;
(f) the titanium oxide is $TiO_2$; and
(g) the zirconium oxide is $ZrO_2$.

2. The cosmetic composition of claim 1, wherein said glass flake composition has a softening point below 800° C.

3. The cosmetic composition of claim 1, wherein said effect pigments comprise at least one layer of low refractive index material and at least one layer of high refractive index material.

4. The cosmetic composition of claim 1, wherein said at least one high refractive material is selected from the group of metal oxides consisting of titanium dioxide, iron oxide, chromium oxide, copper oxide, zinc oxide, tin oxide, vanadium oxide, cobalt oxide, nickel oxide, antimony oxide, lead oxide, silver oxide, molybdenum oxide, tungsten oxide, zirconium oxide, suboxides and mixtures thereof.

5. The cosmetic composition of claim 1, wherein at least one of tin oxide and aluminium oxide is coated between said glass flakes and a subsequent layer of high refractive material.

6. The cosmetic composition of claim 1, wherein said high refractive material is selected from the group of metal sulfides consisting of titanium sulfide, iron sulfide, chromium sulfide, copper sulfide, zinc sulfide, tin sulfide, vanadium sulfide, cobalt sulfide, antimony sulfide, lead sulfide, silver sulfide, molybdenum sulfide, tungsten sulfide, zirconium sulfide, subsulfides and mixtures thereof.

7. The cosmetic composition of claim 3, wherein said low refractive material is selected from the group consisting of low refractive metal oxides.

8. The cosmetic composition of claim 1, wherein said glass flakes are coated with one or more layers of metal oxide selected from the group consisting of $TiO_2$, $Fe_2O_3$ and mixtures thereof.

9. The cosmetic composition of claim 1, wherein the high refractive material is titanium dioxide in the rutile modification.

10. The cosmetic composition of claim 1, wherein the median thickness of the glass flake substrate is 0.05μm to 10μm.

11. The cosmetic composition of claim 7, wherein the median thickness of the glass flake substrate is 0.1μm to 2μm.

12. The cosmetic composition of claim 1 in a form selected from the group consisting of solutions, suspensions, emulsions, PIT emulsions, pastes, ointments, gels, creams, lotions, powders, soaps, surfactant-containing, cleansing preparations, oils, aerosols, sprays, sticks, shampoos and shower compositions.

13. The cosmetic composition of claim 1, wherein the cosmetic composition is selected from the group consisting of a body powder, face powder, pressed powder, loose powder, face make-up, powder cream, cream make up, powder make-up, emulsion make-up, wax make-up, foundation, mousse, rouge or blush, eye make-up, mascara, eyeliner, liquid eyeliner, eyebrow pencil, lip care preparation, lipstick, lip gloss, lip liner, hair care preparation, rinse-off and leave-on hair conditioner, perm, hair setting preparation, hair fixatives, hair mousse, hair gel, hair wax, permanent hair dye, semi-permanent hair dye, temporary hair dye, skin care preparation, body cream, face lotion, face cream, gel, sun care preparation, pre-sun preparations, after-sun preparations, insect repellent, self tanning preparation, nail polish, skin cleansing preparation, face cleansing preparation and face peeling.

14. The cosmetic composition of claim 1, wherein the cosmetic composition is a sun protection formulation further comprising UV filters.

15. The cosmetic composition of claim 1, wherein the cosmetic composition is a nail-care composition.

16. A method of preparing cosmetic formulations for decorative cosmetics or personal care applications, wherein the method comprises including in said formulations the cosmetic composition of claim 1.

17. The cosmetic composition of claim 1, wherein the metal chalcogenides are selected from the group consisting of metal oxides, metal suboxides and metal sulfides.

18. The cosmetic composition of claim 7, wherein the low refractive metal oxide is selected from the group consisting of silica, silica hydrate, silicon oxide hydroxide, silicon oxide hydroxide hydrate, alumina, alumina hydrate, aluminium oxide hydroxide, aluminium oxide hydroxide hydrate, boron oxide, boron hydroxide, magnesium silicate and mixtures thereof.

19. The cosmetic composition of claim 1 wherein the potassium oxide is $K_2O$, the lithium oxide is $Li_2O$ and the magnesium oxide is MgO.

\* \* \* \* \*